United States Patent
Maor

(10) Patent No.: US 7,642,092 B2
(45) Date of Patent: Jan. 5, 2010

(54) CULTURED CARTILAGE/BONE CELLS/TISSUE, METHOD OF GENERATING SAME AND USES THEREOF

(75) Inventor: Gila Maor, Kiryat Motzkin (IL)

(73) Assignee: Technion Research & Development Foundation Ltd., Haifa (IL)

(*) Notice: Subject to any disclaimer, the term of this patent is extended or adjusted under 35 U.S.C. 154(b) by 588 days.

(21) Appl. No.: 10/627,739

(22) Filed: Jul. 28, 2003

(65) Prior Publication Data

US 2004/0175826 A1 Sep. 9, 2004

Related U.S. Application Data

(60) Provisional application No. 60/450,688, filed on Mar. 3, 2003.

(51) Int. Cl.
C12N 5/00 (2006.01)
(52) U.S. Cl. .................. 435/377; 435/375; 435/325
(58) Field of Classification Search .................. None
See application file for complete search history.

(56) References Cited

U.S. PATENT DOCUMENTS

| 4,757,017 | A | * | 7/1988 | Cheung ................. 435/384 |
| 5,541,107 | A | | 7/1996 | Naughton et al. |
| 5,723,331 | A | * | 3/1998 | Tubo et al. ............. 435/366 |
| 5,842,477 | A | | 12/1998 | Naughton et al. |
| 5,902,741 | A | | 5/1999 | Purchio et al. |
| 6,365,405 | B1 | | 4/2002 | Salzmann et al. |

OTHER PUBLICATIONS

Bhalerao J et al. 1995. Establishment and characterization of two clonal cell lines derived from murine mandibular condyles. Tissue and Cell 27: 369-382.*
Landesberg R et al. 1995. The mandibular condylar growth center: separation and characterization of the cellular elements. Calcif Tissue Int 56: 71-77.*
Palmer G et al. 2002. Production of interleukin-1 receptor antagonist by human articular chondrocytes. Arthritis Research 4: 226-231; obtained online and including supplementary material, 8 pages total.*
Schnabel M et al. 2002. Dedifferentiation-associated changes in morphology and gene expression in primary human articular chondrocytes in cell culture. Osteoarthritis and Cartilage 10: 62-70.*
Visnapuu et al, "Distribution and characterization of proliferative cells in the rat mandibular condyle during growth" *Eur J Orthod.* Dec. 2000;22(6):631-8. Erratum in: *Eur J Orthod* Aug. 2001;23(4):473.
Deleersnijder et al, "Isolation of markers for chondro-osteogenic differentiation using cDNA library subtraction. Molecular cloning and characterization of a gene belonging to a novel multigene family of integral membrane proteins" *J Biol Chem.* Aug. 9, 1996;271(32):19475-82.
Kimura et al, "Chondrocytes embedded in collagen gels maintain cartilage phenotype during long-term cultures", *Clin Orthop.* Jun. 1984(186):231-9.
Enomoto-Iwamoto, M. et al., "Involvement of alpha5beta1 integrin in matrix interactions and proliferation of chondrocytes" *J Bone Miner Res.* Jul. 1997;12(7):1124-32.
Liu et al, "Re-expression of differentiated proteoglycan phenotype by dedifferentiated human chondrocytes during culture in alginate beads", *Biochim Biophys Acta*: Nov. 27, 1997;1425(3):505-15. (Abstract).
Takigawa et al, "Chondrocytes dedifferentiated by serial monolayer culture form cartilage nodules in nude mice", J. Bone Miner. Sep. 1987;2(6):449-62 (Abstract).
Miura et al, "Extracellular matrix environment influences chondrogenic pattern formation in limb bud micromass culture: experimental verification of theoretical models", Anat Rec. Jan. 1, 2000;258(1):100-7. (Abstract).
Shakibaei et al, "Differentiation of mesenchymal limb bud cells to chondrocytes in alginate beads", *Cell Biol Int.* Feb. 1997;21(2):75-86. (Abstract).
Martin et al, "Mammalian chondrocytes expanded in the presence of fibroblast growth factor 2 maintain the ability to differentiate and regenerate three-dimensional cartilaginous tissue", *Exp Cell Res.* Dec. 15, 1999;253(2):681-8. (Abstract).
Benya et al, "Dihydrocytochalasin B enhances transforming growth factor-beta-induced reexpression of the differentiated chondrocyte phenotype without stimulation of collagen synthesis", Exp Cell Res. Feb. 1993;204(2):268-77. (Abstract).
Takigawa et al, "Studies on chondrocytes from mandibular condylar cartilage, nasal septal cartilage, and spheno-occipital synchondrosis in culture. I. Morphology, growth, glycosaminoglycan synthesis, and responsiveness to bovine parathyroid hormone (1-34)", J Dent Res. Jan. 1984;63(1):19-22. (Abstract).

* cited by examiner

*Primary Examiner*—Lora E Barnhart

(57) ABSTRACT

A method of generating cultured chondrocytes/endochondral bone cells is provided. The method comprising isolating chondrocytes from mandibular condyle tissue, and culturing the isolated chondrocytes. A method of isolating chondrocytes from mandibular condyle tissue is further provided. The method comprises isolating mandibular condyle tissue from a mammal and treating the mandibular condyle tissue so as to selectively remove fibroblast-like cells and/or myocytes therefrom, the modified mandibular condyle tissue including chondrocytes, and selectively collecting the chondrocytes from the modified mandibular condyle tissue.

11 Claims, 8 Drawing Sheets
(7 of 8 Drawing Sheet(s) Filed in Color)

Fig. 1a            Fig. 1b
 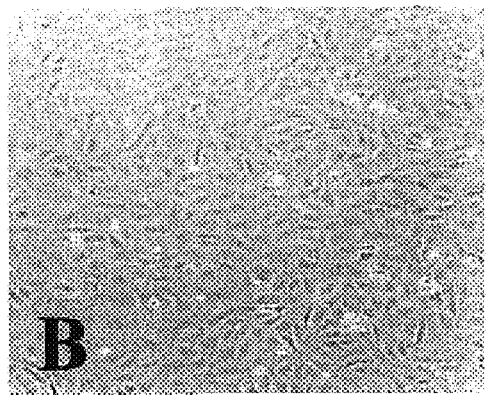
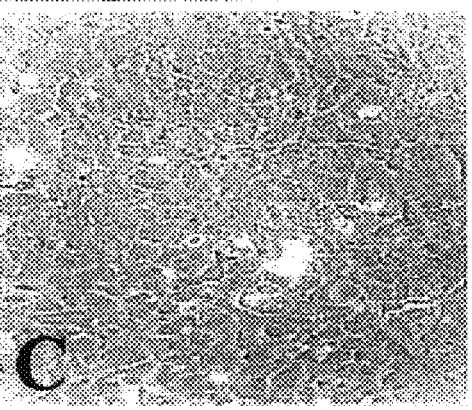 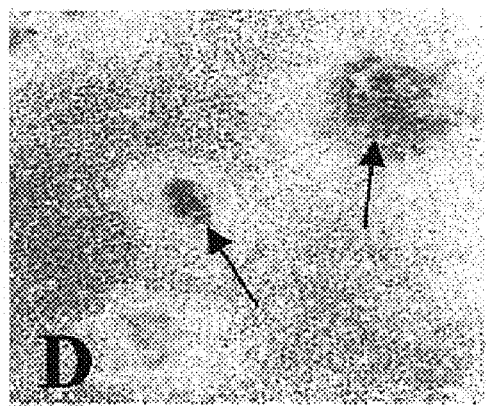
Fig. 1c            Fig. 1d Fig. 6a Fig. 6b
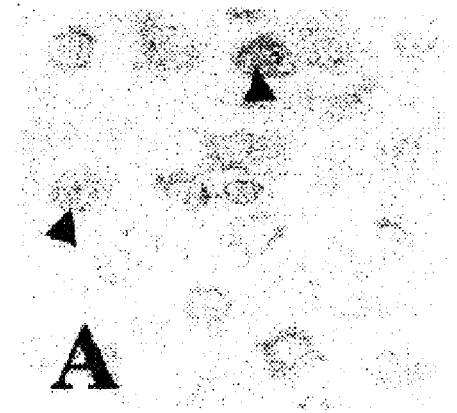
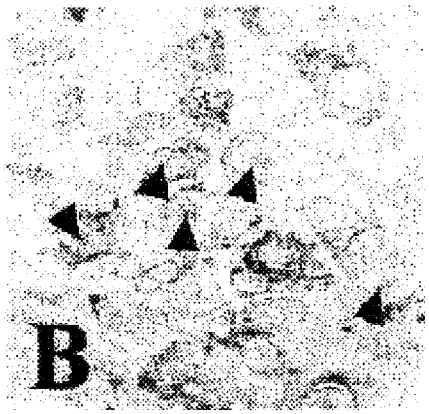
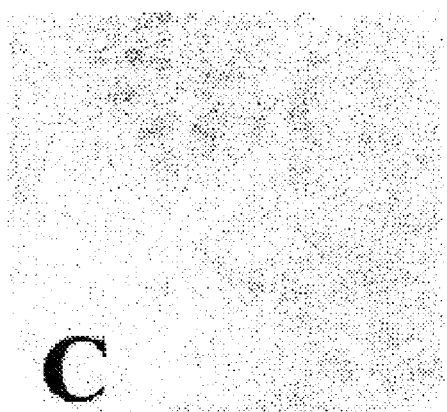
Fig. 6c Fig. 6d

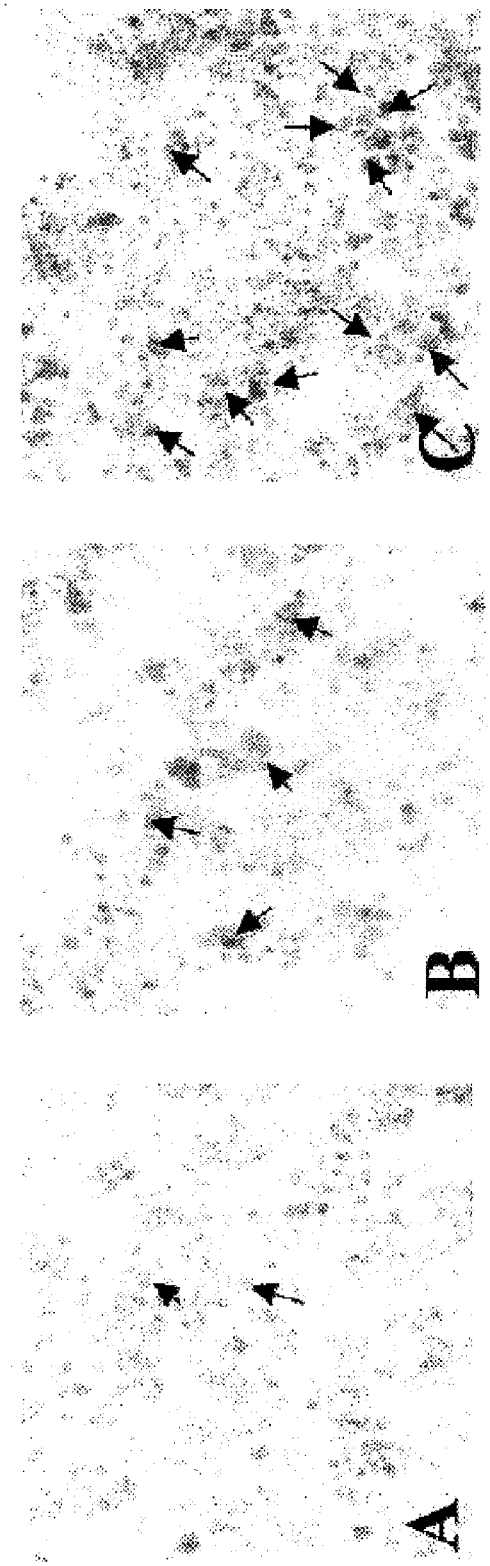

SEQUENCE LISTING

<160> NUMBER OF SEQ ID NOS: 5

<210> SEQ ID NO 1
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 1
gagggcacaa gttctatctg ga                                          22

<210> SEQ ID NO 2
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 2
gagatttgtg ggccggagcg g                                           21

<210> SEQ ID NO 3
<211> LENGTH: 633
<212> TYPE: DNA
<213> ORGANISM: Mus musculus

<400> SEQUENCE: 3
gagggcacaa gttctatctg gaaaaaaaag gagggactat ggcgtcaaac agcctcttca    60
gcgcagtgac accgtgtcag caaagcttct tttgggatcc gagcaccagc cggcgcttca   120
gccccccctc cagcagcctg cagcccggca agatgagcga cgtgagcccg gtggtggctg   180
cgcagcagca gcaacagcag cagcagcagc agcaacagca gcagcaacaa cagcaacagc   240
aacaacagca gcagcagcag cagcagcagg aggcggccgc agcagcagcg gcggcagcgg   300
cggcggcagc agcggcggcg gccgcagtgc cccgattgag gccgccgcac gacaaccgca   360
ccatggtgga gatcatcgcg gaccacccgg ccgaactggt ccgcaccgac agtcccaact   420
tcctgtgctc cgtgctgccc tcgcactggc ggtgcaacaa gaccctgccc gtggccttca   480
aggttgtagc cctcggagag gtaccagatg ggactgtggt taccgtcatg gccgggaatg   540
atgagaacta ctccgccgag ctccgaaatg cctccgctgt tatgaaaaac caagtagcca   600
ggttcaacga tctgagattt gtgggccgga gcg                               633

<210> SEQ ID NO 4
<211> LENGTH: 633
<212> TYPE: RNA

```
<213> ORGANISM: Artificial sequence
<220> FEATURE:
<223> OTHER INFORMATION: Cbfa1 antisense RNA transcript

<400> SEQUENCE: 4
cgcuccggcc cacaaaucuc agaucguuga accuggcuac uugguuuuuc auaacagcgg      60
aggcauuucg gagcucggcg gaguaguucu caucauuccc ggccaugacg guaaccacag     120
ucccaucugg uacucuccg agggcuacaa ccuugaaggc cacgggcagg gucuuguugc      180
accgccagug cgagggcagc acggagcaca ggaaguuggg acugucggug cggaccaguu     240
cggccgggug guccgcgaug aucuccacca uggugcgguu gucgugcggc ggccucaauc     300
ggggcacugc ggccgccgcc gcugcugccg ccgccgcugc cgccgcugcu gcugcggccg     360 ccuccgcug cugcugcugc ugcugcuguu guugcuguug cuguuguugc ugcugcuguu     420
gcugcugcug cugcugcugu ugcugcugcu gcgcagccac caccgggcuc acgucgcuca     480
ucuugccggg cugcaggcug cuggaggggg ggcugaagcg ccggcuggug cucggauccc     540
aaaagaagcu uugcugacac ggugucacug cgcugaagag gcuguuugac gccauagucc     600
cuccuuuuuu uuccagauag aacuugugcc cuc                                 633

<210> SEQ ID NO 5
<211> LENGTH: 633
<212> TYPE: RNA
<213> ORGANISM: Artificial sequence
<220> FEATURE:
<223> OTHER INFORMATION: Sense RNA probe

<400> SEQUENCE: 5
gagggcacaa guucuaucug gaaaaaaaag gagggacuau ggcgucaaac agccucuuca      60
gcgcagugac accgugucag caaagcuucu uuugggaucc gagcaccagc cggcgcuuca     120 gccccccuc cagcagccug cagcccggca agaugagcga cgugagcccg guggugcug       180 cgcagcagca gcaacagcag cagcagcagc agcaacagca gcagcaacaa cagcaacagc     240
aacaacagca gcagcagcag cagcagcagg aggcggccgc agcagcagcg gcggcagcgg     300
cggcggcagc agcggcggcg gccgcagugc cccgauugag gccgccgcac gacaaccgca     360
ccauggugga gaucaucgcg gaccacccgg ccgaacuggu ccgcaccgac aguccaacu      420 uccugugcuc cgugcugccc ucgcacuggc ggugcaacaa gacccugccc guggccuuca     480
agguuguagc ccucggagag guaccagaug ggacuguggu uaccgucaug gccgggaaug     540
augagaacua cuccgccgag cuccgaaaug ccuccgcugu uaugaaaaac caaguagcca     600
gguucaacga ucugagauuu gugggccgga gcg                                 633
```

CULTURED CARTILAGE/BONE CELLS/TISSUE, METHOD OF GENERATING SAME AND USES THEREOF

This application claims the benefit of priority from U.S. Provisional Patent Application No. 60/450,688, filed Mar. 3, 2003, the contents of which are hereby incorporated by reference.

FIELD AND BACKGROUND OF THE INVENTION

The present invention relates to methods of isolating chondrocytes, methods of culturing isolated chondrocytes to generate cultured chondrocytes/bone cells, and to uses of such cultured chondrocytes/bone cells. More particularly, the present invention relates to methods of isolating mandibular condyle chondrocytes, methods of culturing same to generate highly differentiated cultured chondrocytes/endochondral bone cells, and to uses of such cultured chondrocytes/endochondral bone cells for treating cartilage/bone diseases.

Cartilage/bone diseases include highly debilitating and/or lethal diseases such as arthritis, articular cartilage injury, meniscal disorders, joint infections, chondrogenesis disorders and cosmetic disorders of cartilaginous structures of the body for which no optimal therapies are currently available. Failure of diarthrodial joints leads to arthritis, the most common form being osteoarthritis. Repair of arthritic joints requires orthopedic surgery to replace the worn-out joints by a prosthesis or by a biological graft. Arthritis alone is an enormous medical and economic problem, with more than thirty million Americans suffering from this highly debilitating disease.

Articular joints, of which various types exist in the body, are a vital component of the musculoskeletal system. Freely moving joints (ankle, elbow, hip, knee, shoulder, and those of the fingers, toes and wrist) are known as diarthrodial or synovial joints and are critical for body movement. The intervertebral joints of the spine, which are not diarthrodial joints as they are fibrous and static, critically provide the flexibility required by the spine. Diarthrodial joints enable local motion and other activities of daily life to take place. They perform their function so well that we are often not even aware of their existence nor the function they provide until injury strikes or arthritis develops. From an engineering point of view, these natural bearings are very uncommon structures. Under healthy and ideal conditions, their function is nearly frictionless and they remain almost entirely wear-resistant throughout life. Diarthrodial joints share common structural features, notably including their being enclosed in a strong fibrous capsule. The inner surfaces of the joint capsule are lined with a metabolically active tissue, the synovium, which secretes the synovial fluid that lubricates the joint and provides the nutrients required by the avascular cartilage. The articulating bone ends in the joint are lined with a thin layer of hydrated soft tissue known as articular cartilage. These linings, the synovium and articular cartilage layers, form the joint cavity which contains the synovial fluid. Thus, in animal joints, the synovial fluid, articular cartilage, and the supporting bone form the bearing system which provides the smooth nearly-frictionless bearing system of the body. While diarthrodial joints are subjected to an enormous range of loading conditions under cyclical conditions, the cartilage surfaces undergo little wear and tear under normal circumstances. Indeed, most human joints must be capable of functioning effectively under very high loads and stresses and at very low operating speeds. These performance characteristics demand efficient lubrication processes to minimize friction and wear of cartilage in the joint. The joint is stabilized by, and in motion is controlled by, ligaments and tendons which may be inside or outside the joint capsule. Breakdown of the joint cartilage as a result of autoimmune, physical, chemical and/or infectious insult leads to arthritis.

Hyaline cartilage, the most abundant form of cartilage, is glass smooth, glistening and bluish white in appearance, although older or diseased tissue tends to lose this appearance. The most common hyaline cartilage, and the most studied, is the articular cartilage. This tissue covers the articulating surfaces of bones within diarthrodial joints. Articular cartilage is characterized by a particular structural organization, consisting of specialized cartilage cells termed "chondrocytes" embedded in an intercellular material, typically referred to as "cartilage matrix", which is rich in proteoglycans, collagen fibrils, other proteins, and water. While cartilage tissue is neither innervated nor penetrated by the vascular or lymphatic systems, in the mature joint of adults, the underlying subchondral bone tissue—which forms a narrow, continuous plate between the bone tissue and the cartilage—is innervated and vascularized. Beneath this bone plate, the bone tissue forms trabeculae, containing the marrow. In immature joints, articular cartilage is underlined by only primary bone trabeculae. A portion of the meniscal tissue in joints (referred to as the "interarticular" cartilage) also consists of cartilage whose make-up is similar to articular cartilage. It is generally believed that because articular cartilage lacks a vasculature, damaged cartilage tissue does not receive sufficient or proper stimuli to elicit a repair response.

The menisci of the knee, and other similar structures such as the disc of the temporomandibular joint and the labrum of the shoulder, are specialized fibrocartilagenous structures which perform functions which are vital for normal joint function. They are known to function in assisting the articular cartilage in distributing loads across the joint, assisting the ligaments and tendons in providing joint stability, playing a major role in shock absorption, and possibly in assisting lubrication of the joint. The menisci, disc and labrum are hydrated fibrocartilage structures composed primarily of collagen (type I) with smaller amounts of other collagens and proteoglycans (including aggrecan and the smaller, non-aggregating proteoglycans). They contain a sparse population of cells which, like the chondrocytes of cartilage, are responsible for the synthesis and maintenance of this extracellular matrix. Damage to these structures can lead to a reduction in joint function and degeneration of the articular cartilage, and surgical removal of such damaged structures, usually the main treatment, can result in early onset of osteoarthritis.

Skeletal ligaments are specialized connective tissues that connect bones. They serve a passive mechanical function in stabilizing joints and in guiding joint motion. Further, they may have a neurosensory role transporting dynamic information to muscles. Ligaments are composed primarily of type I collagen organized in parallel arrays, with small amounts of other collagens, proteoglycans, elastin and other proteins and glycoproteins. The cells are fibroblastic in the midsubstance, and appear more chondroid at and near the insertion sites. Tendons have a similar structure, with a relatively high concentration of collagen, organized primarily as fibers in parallel. Other components are proteoglycans, elastin and other proteins and glycoproteins. The cells are fibroblastic in nature. The cells of the tendon and ligament are metabolically active and are responsible for the synthesis and maintenance of this extracellular matrix.

Proteoglycans comprise the second largest portion of the organic material in articular cartilage. These macromolecules are composed of a protein core to which are attached a number of covalently bound glucosaminoglycan (GAG) chains, such as chondroitin sulfate and keratan sulfate. There are many different types of proteoglycans present in a wide range of tissues throughout the body; presumably, they also have different functions in the various tissues. However, the most extensively studied proteoglycans have been those from articular cartilage because of their role in regulating skeletal growth, joint function and the development of arthritis.

The major proteoglycans present in articular cartilage are the large aggregating type (50-85%) and the large non-aggregating type (10-40%) with distinct small proteoglycans also present. The molecular weights of these proteoglycan monomers range from 1,000-4,000 kDa, and they contribute significantly to the mechanical and physicochemical properties of cartilage. These molecules are highly ordered structures with length scales ranging from 0.01-1 microns. Proteoglycans comprise an extended protein core with several distinct regions, including an N-terminal region with two globular domains (G1 and G2), a keratan sulfate-rich domain, a longer chondroitin sulfate-rich domain which may also contain some interspersed keratan sulfate and neutral oligosaccharide chains, and a C-terminal globular domain (G3) on the proteoglycan monomer. Aggregates are formed when many proteoglycan monomers bind to a long monofilament chain of hyaluronan via their G1 globular domain. Each proteoglycan-hyaluronan bond is stabilized by a separate 41-48 kDa globular link protein. The structure of proteoglycan in cartilage is not uniform. Differences in chain length and amounts of keratan sulfate and chondroitin sulfate, length of the protein core, and degree of aggregation all contribute to the compositional and structural heterogeneities of proteoglycans within cartilage.

The GAG chains of the proteoglycans afford important physicochemical properties to cartilage. First, chondroitin sulfate which has a molecular weight of about 20 kDa is composed of repeating disaccharide units of glucuronic acid and N-acetylgalactosamine with one sulfate ($SO_4$) group and one carboxyl (COOH) group per disaccharide. Evidence exists indicating that these chondroitin sulfate chains are the main determinants of frictional resistance against interstitial fluid flow. Keratan sulfate consists of repeating disaccharide units of galactose and N-acetylglucosamine, again averaging approximately one sulfate group per disaccharide. The keratan sulfate content of proteoglycans progressively increases with age from fetal to senescent cartilage. Both proteoglycan content and size decrease with increasing severity of osteoarthritis.

In articular cartilage, molecular interactions occur through collagen-collagen covalent cross-link interactions, and proteoglycan-proteoglycan and collagen-proteoglycan non-covalent (electrostatic and mechanical) interactions. The best-known interactions are the collagen-collagen covalent cross-links which are important in providing a strong and stiff collagen network. Thus, in the extracellular matrix these two molecular networks (proteoglycan and collagen) must coexist to form a fiber-reinforced composite solid with the collagen network providing the tensile stiffness and strength, and the proteoglycan network providing the compressive stiffness. The physical interactions between collagen and proteoglycan can arise from two sources: electrostatic and mechanical. First, evidence exists indicating that the negative charge groups on the proteoglycans can interact with the positive charge groups along the collagen fibrils, and hyaluronates of the aggregate do interact with type II, IX and X collagen. Second, evidence of strong frictional interaction between the proteoglycans and the fine collagen network also exists. No covalent bonding exists between collagen fibrils and proteoglycans. In normal cartilaginous tissue, proteoglycans are slowly but continuously turned over, the degraded molecules are released from the cartilage and are replaced by newly synthesized components. It is the coordinate control of synthesis and degradation of the matrix components by the chondrocytes that maintain normal cartilage. In experimental models of joint disease, for example, there is evidence of charges in the rate of biosynthesis and turnover of proteoglycans, which may contribute to cartilage degeneration. This chondrocyte-mediated degeneration leads to the whole cascade of degenerative bone and connective tissue events that results in osteoarthritis, limb immobilization, and other effects requiring surgical intervention. Degenerative loss of articular cartilage, for example, at the acetabular/femoral head articulation, results in heavy loading of the soft tissue, and can require radical surgery.

Chondrogenesis is vital to postnatal skeletal growth which occurs mainly by endochondral bone formation, a highly regulated multistep process. The skeletal cellular population follows a cascade of events that includes proliferation of precursor cells, differentiation into chondroblasts, maturation of chondrocytes, hypertrophy, and apoptosis [Chen, Q. et al., 1995. Dev Biol. (N.Y. 1985) 172:293-309]. These processes are accompanied by the synthesis of specific matrix proteins such as cartilage proteoglycans and type II collagen, which are secreted by mature chondrocytes, and type X collagen, which is secreted by hypertrophic chondrocytes (Beier, F. et al., 1999. J Cell Biochem 72:549-557). The sustenance of the differentiated state of the chondrocytes is dependent on close cell-matrix interactions (Svoboda, K. K., 1998. Microsc Res Tech. 43:111-122), such that releasing the cells from their cartilaginous environment results in a rapid loss of their phenotypic morphology and function (von der Mark, K. et al., 1977. Nature 267:531-532). Normal chondrogenesis is a complex process controlled by a combination of systemic and local factors such as growth hormone, thyroid and parathyroid hormones, and, during various developmental stages, also by insulin and sex hormones, the neonatal period and adolescence, respectively (Amizuka, N. et al., 1994. J. Cell Biol. 126:1611-1623; Greenspan, S. L. and Greenspan, F. S., 1999. Ann Intern Med 130:750-758; Maor, G. et al., 1999. Endocrinology 140:1901-1910; Menon, R. K. and Sperling, M. A., 1996. Endocrinol Metab Clin North Am 25(3):633-647; Spagnoli, A. and Rosenfeld, R. G., 1996. Endocrinol Metab Clin North Am 25:615-631). Insulin-like growth factor-I (IGF-I) is the principal local growth factor of chondrogenesis and skeletal growth and acts in an auto/paracrine fashion (Isgaard, J., 1992. Growth Regul 2:16-22).

As described hereinabove, cartilage/bone diseases are of tremendous medical and economic impact, and hence there is an obvious and urgent need for novel and improved methods of treating such diseases.

For example, over one million surgical procedures in the United States each year involve cartilage replacement. Current therapies include transplantation with allografts (removing healthy cartilage from a donor, and reimplanting it into a joint of the recipient), implantation of artificial polymer or metal prostheses, and surgical removal of old or degenerative cartilage and the surgical treatment of underlying bone to stimulate new cartilage formation. This new cartilage is usually a fibrous cartilage significantly inferior to the hyaline cartilage it is replacing. Other surgical procedures of synovial joints involve the replacement of menisci, ligaments and tendons with biological grafts or artificial tissues. Torn or severed menisci, discs of the temporomandibular joint, labrum of the shoulder, tendons and ligaments often undergo surgical repair.

Surgical procedures account for only a fraction of the treatment of individuals who suffer from disabling diseases resulting from connective tissue damage and degeneration in synovial joint. Alternative treatment includes conservative treatment (e.g., rest and physical therapy), and treatment is largely directed at symptomatic relief through the use of analgesics and nonsteroidal anti-inflammatory drugs.

There are significant limitations with all present approaches. Artificial prostheses have a limited lifetime, and can fail prematurely. Recurrent replacements of prostheses is not an advisable treatment, and, therefore, the relatively young and active patient is often consigned to slow joint degeneration until the use of prosthetic implants becomes a reasonable clinical option. Prostheses rarely replicate the performance of the original tissue. A prosthesis cannot adapt in response to environmental stress as does a biological tissue, nor can it repair itself. Biological allograft material is in limited supply, appropriate size shape and tissue type are difficult to obtain, and has the risk of carrying infectious diseases. Use of autograft material compromises the site used for the source tissue (e.g., using patella tendon to replace anterior cruciate ligament), and can only offer this tissue once.

In light of the above described drawbacks of classical treatment methods, an optimal strategy for treating cartilage/bone diseases, would be to utilize cultured cartilage/bone to repair or replace cartilage/bone lost or damaged as a result of disease or injury. Such an approach would be optimal since cultured cartilage/bone could theoretically be produced with essentially any desired characteristics and in essentially any desired quantity. However, culturing cartilage/bone from primary chondrocytes has been found to be highly problematic due to the fact that primary cartilage-derived cell cultures undergo dedifferentiation, acquire fibroblastic features, and lose most of the characteristics of mature chondrocytes. This phenomenon is due mainly to the loss in culture of the close matrix-cell interrelationship typical of cartilage tissue, which, as described above, is a vital element of cartilage formation and homeostasis. This dedifferentiation phenomenon is furthermore a serious obstacle for ex-vivo studies of the endochondral ossification process and its extra- and intracellular regulation, and for in-vitro studies of various articular pathologies such as rheumatoid arthritis or osteoarthritis.

Several prior art approaches have been employed or suggested in order to optimally generate cultured cartilage/bone.

One approach involves culturing limb mesenchyme in micromass cultures in three-dimensional collagen and agarose gels (Miura, T. and Shiota, K., 2000. Anat Rec. 258:100-107).

Another approach involves culturing isolated cells of mouse limb bud mesenchyme (Shakibaei, M. and De Souza, P., 1997. Cell Biol Int 21:75-86), or dedifferentiated human articular chondrocytes (Liu, H. et al., 1998. Biochim Biophys Acta 1425:505-515) in alginate beads.

Yet another approach involves culturing rabbit growth plate chondrocytes in soft agar, or on a substrate coated with type I collagen, type II collagen or fibronectin (Enomoto-Iwamoto, M. et al., 1997. J Bone Miner Res 12:1124-1132).

Still another approach involves culturing primary chondrocytes in the presence of fibroblast growth factor (FGF)-2 in three-dimensional polymer scaffolds (Martin, I. et al., 1999. Exp Cell Res 253:681-688).

A further approach involves culturing dedifferentiated rabbit articular chondrocytes in the presence of transforming growth factor (TGF)-beta 1, with or without the microfilament modifying drug dihydrocytochalasin B (DHCB; Benya, P. D. and Padilla, S. R., 1993. Exp Cell Res 204:268-277).

Yet a further approach involves culturing primary chondrocytes (Borge, L. et al., 1997. In-vitro Cell Dev Biol Anim 33:703-709), mesenchyme of chick embryo wing bud in micromass cultures (Kulyk, W. M. et al., 2000. Exp Cell Res 255:327-332), or fibroblasts under hypoxic conditions (U.S. Pat. No. 6,489,165) in the presence of the protein kinase C (PKC)/actin polymerization antagonist staurosporine.

Still a further approach involves culturing mesenchymal progenitor cells using chemically defined components (U.S. Pat. Application No. 20030026786).

All of the aforementioned approaches, however, suffer from significant disadvantages including: incapacity to generate cultured cartilage/bone displaying optimal cartilage/bone specific differentiation, and/or displaying such differentiation for an optimally long duration in-vitro; and/or their being excessively cumbersome/complex and/or expensive to practice, such as in the case of approaches involving the use of three dimensional supports or biomolecule-coated substrates.

Thus, all prior art approaches have failed to provide an adequate solution for generating cultured cartilage/bone.

There is thus a widely recognized need for, and it would be highly advantageous to have, a method of generating cultured cartilage/bone devoid of the above limitation.

SUMMARY OF THE INVENTION

According to one aspect of the present invention there is provided an isolated mandibular condyle tissue comprising chondrocytes and being depleted of fibroblast-like cells and/or myocytes.

According to further features in preferred embodiments of the invention described below, the mandibular condyle tissue is mostly or completely depleted of fibroblast-like cells and/or myocytes.

According to another aspect of the present invention there is provided a method of isolating chondrocytes from mandibular condyle tissue, the method comprising the steps of: isolating mandibular condyle tissue from a mammal and treating the mandibular condyle tissue so as to selectively remove fibroblast-like cells and/or myocytes therefrom, thereby generating modified mandibular condyle tissue depleted of the fibroblast-like cells and/or the myocytes, the modified condyle tissue including chondrocytes; and selectively harvesting the chondrocytes from the modified condyle tissue, thereby isolating chondrocytes from mandibular condyle tissue.

According to further features in preferred embodiments of the invention described below, treating the mandibular condyle tissue so as to selectively remove fibroblast-like cells and/or myocytes therefrom is effected by incubating the mandibular condyle tissue with a protease.

According to yet another aspect of the present invention there is provided a cell culture comprising isolated chondrocytes being capable of generating endochondral bone cells when cultured under culturing conditions which: include a two dimensional support not coated with a biomolecule; and a culture medium devoid of a supplement selected from the group consisting of a microfilament-modifying compound, a protein kinase inhibitor and a polypeptide growth factor, the supplement not being derived from a serum supplement of the culture medium.

As used herein, the term "endochondral bone cell", refers to a cell of any cell type normally found in endochondral bone, including endochondral bone precursor cells, osteoblasts, hypertrophic cells, mature chondrocytes and chondroblasts.

According to further features in preferred embodiments of the invention described below, the culture medium includes at least one supplement selected from the group consisting of ascorbic acid, beta-glycerophosphate, pyruvate and IGF-I.

According to still further features in the described preferred embodiments, the culturing conditions are normoxic.

According to still further features in the described preferred embodiments, the culturing conditions further include culturing a subconfluent population of the isolated chondrocytes.

According to still further features in the described preferred embodiments, the isolated chondrocytes are capable of generating the endochondral bone cells when cultured for a minimum duration selected from a range of 14-21 days.

According to still further features in the described preferred embodiments, the isolated chondrocytes are derived from mandibular condyle tissue.

According to still another aspect of the present invention there is provided a method of redifferentiating dedifferentiated chondrocytes, the method comprising culturing dedifferentiated chondrocytes under culturing conditions which comprise a culture medium including at least one supplement selected from the group consisting of ascorbic acid, beta-glycerophosphate, pyruvate and IGF-I, the culturing conditions being devoid of a three dimensional support and/or of a biomolecule-coated support, thereby redifferentiating the dedifferentiated chondrocytes.

According to further features in preferred embodiments of the invention described below, the culture medium is devoid of at least one supplement selected from the group consisting of a microfilament-modifying compound, a protein kinase inhibitor, and a polypeptide growth factor, wherein the supplement selected from the group consisting of a microfilament-modifying compound, a protein kinase inhibitor, and a polypeptide growth factor is not derived from a serum supplement of the culture medium.

According to still further features in the described preferred embodiments, the culturing conditions further comprise culturing a subconfluent population of the dedifferentiated chondrocytes.

According to still further features in the described preferred embodiments, the culturing is effected for a minimum duration selected from a range of 1-6 days.

According to still further features in the described preferred embodiments, the dedifferentiated chondrocytes are derived from mandibular condyle tissue.

According to a further aspect of the present invention there is provided a method of treating a cartilage/bone disease in a subject, the method comprising the steps of: isolating chondrocytes from mandibular condyle tissue; culturing the isolated chondrocytes, thereby generating cultured chondrocytes; and administering a therapeutically effective dose of the cultured chondrocytes to the subject, thereby treating the cartilage/bone disease in the subject.

According to further features in preferred embodiments of the invention described below, the method of treating a cartilage disease further comprises isolating the cultured chondrocytes prior to administering the therapeutically effective dose of the cultured chondrocytes to the subject.

According to still further features in the described preferred embodiments, the step of culturing the isolated chondrocytes is effected using culturing conditions devoid of a three dimensional support.

According to still further features in the described preferred embodiments, the step of culturing the isolated chondrocytes is effected using culturing conditions devoid of a biomolecule-coated support.

According to still further features in the described preferred embodiments, the step of culturing the isolated chondrocytes is effected using culturing conditions which comprise a culture medium including at least one supplement selected from the group consisting of ascorbic acid, beta-glycerophosphate, pyruvate and IGF-I.

According to still further features in the described preferred embodiments, the step of culturing the isolated chondrocytes is effected using culturing conditions including a culture medium devoid of at least one supplement selected from the group consisting of a microfilament-modifying compound, a protein kinase inhibitor, and a polypeptide growth factor, wherein the supplement is not derived from a serum supplement of the culture medium.

According to still further features in the described preferred embodiments, the step of culturing the isolated chondrocytes is effected using culturing conditions which are normoxic.

According to still further features in the described preferred embodiments, the step of culturing the isolated chondrocytes is effected using culturing conditions which include culturing a subconfluent population of the isolated chondrocytes.

According to still further features in the described preferred embodiments, the step of culturing the isolated chondrocytes is effected for a minimum duration selected from a range of 5-21 days.

According to still further features in the described preferred embodiments, the step of culturing the isolated chondrocytes includes passaging said cultured chondrocytes a predetermined minimum number of times.

According to still further features in the described preferred embodiments, the predetermined minimum number of times is four times.

According to still a further aspect of the present invention there is provided a method of generating cultured chondrocytes, the method comprising the steps of: isolating chondrocytes from mandibular condyle tissue; and culturing the isolated chondrocytes, thereby generating cultured chondrocytes.

According to still further features in the described preferred embodiments, the step of culturing the isolated chondrocytes is effected for a minimum duration selected from a range of 5-21 days.

According to further features in preferred embodiments of the invention described below, the method of generating cultured chondrocytes further comprises passaging the cultured chondrocytes a predetermined minimum number of times.

According to still further features in the described preferred embodiments, the predetermined minimum number of times is four times.

According to an additional aspect of the present invention there is provided a method of generating cultured endochondral bone cells, the method comprising the steps of: isolating chondrocytes from mandibular condyle tissue; and culturing the isolated chondrocytes under conditions suitable for formation of endochondral bone cells, thereby generating cultured endochondral bone cells.

According to further features in preferred embodiments of the invention described below, the step of isolating chondrocytes from mandibular condyle tissue comprises the steps of: selectively removing fibroblast-like cells and/or myocytes from the mandibular condyle tissue, thereby generating modified mandibular condyle tissue depleted of the fibroblast-like cells and/or the myocytes, the modified condyle tissue including chondrocytes; and selectively harvesting the chondrocytes from the modified condyle tissue.

According to still further features in the described preferred embodiments, selectively removing fibroblast-like cells and/or myocytes from the mandibular condyle tissue is effected by incubating the mandibular condyle tissue with a protease.

According to still further features in the described preferred embodiments, selectively harvesting the chondrocytes from the modified condyle tissue is effected by incubating the modified mandibular condyle tissue with a protease so as to selectively release chondrocytes therefrom.

According to still further features in the described preferred embodiments, the step of incubating the modified mandibular condyle tissue with a protease so as to selectively release chondrocytes therefrom further comprises isolating the chondrocytes released from the modified mandibular condyle tissue.

According to still further features in the described preferred embodiments, the step of culturing the isolated chondrocytes is effected using culturing conditions devoid of a three dimensional support.

According to still further features in the described preferred embodiments, the step of culturing the isolated chondrocytes is effected using culturing conditions devoid of a a biomolecule-coated support.

According to still further features in the described preferred embodiments, the three dimensional support is selected from the group consisting of a bead matrix, a gel, a polymer scaffold and a semi-solid substance.

According to still further features in the described preferred embodiments, the biomolecule is selected from the group consisting of a polypeptide, an extracellular matrix component, collagen, type I collagen, type II collagen and fibronectin.

According to still further features in the described preferred embodiments, the step of culturing the isolated chondrocytes is effected using culturing conditions which comprise a culture medium including at least one supplement selected from the group consisting of ascorbic acid, beta-glycerophosphate, pyruvate and IGF-I.

According to still further features in the described preferred embodiments, the step of culturing the isolated chondrocytes is effected using culturing conditions including a culture medium devoid of at least one supplement selected from the group consisting of a microfilament-modifying compound, a protein kinase inhibitor, and a polypeptide growth factor, wherein the supplement is not derived from a serum supplement of the culture medium.

According to still further features in the described preferred embodiments, the microfilament-modifying compound is selected from the group consisting of dihydrocytochalasin B, staurosporine, and an actin filament-modifying compound.

According to still further features in the described preferred embodiments, the protein kinase inhibitor is staurosporine and/or a PKC inhibitor.

According to still further features in the described preferred embodiments, the polypeptide growth factor is selected from the group consisting of TGF, FGF, and IGF.

According to still further features in the described preferred embodiments, the TGF is TGF-beta 1.

According to still further features in the described preferred embodiments, the FGF is FGF-2.

According to still further features in the described preferred embodiments, the IGF is IGF-I.

According to still further features in the described preferred embodiments, the step of culturing the isolated chondrocytes is effected using culturing conditions which are normoxic.

According to still further features in the described preferred embodiments, the step of culturing the isolated chondrocytes is effected using culturing conditions which include culturing a subconfluent population of the isolated chondrocytes.

According to still further features in the described preferred embodiments, the step of culturing the isolated chondrocytes is effected for a minimum duration selected from a range of 14-21 days.

According to still further features in the described preferred embodiments, the mandibular condyle tissue is derived from a mammal.

The present invention successfully addresses the shortcomings of the presently known configurations by providing: (i) a method of generating cultured chondrocytes/endochondral bone cells by culturing mandibular condyle chondrocytes under culturing conditions which are devoid of a three dimensional support and/or of a biomolecule coated support, and which employ a culture medium devoid of a microfilament-modifying compound supplement, a protein kinase inhibitor supplement, and/or a polypeptide growth factor supplement, where such a supplement is not derived from a serum supplement of the culture medium; (ii) a method of treating a cartilage/bone disease in a subject by isolating chondrocytes from mandibular condyle tissue, culturing the isolated chondrocytes so as to generate cultured chondrocytes/endochondral bone cells, and administering a therapeutically effective dose of the cultured chondrocytes/endochondral bone cells to the subject; (iii) a cell culture comprising isolated chondrocytes capable of generating endochondral bone cells when cultured under culturing conditions which include a two dimensional support not coated with a biomolecule, and a culture medium devoid of a non-serum derived supplement such as a microfilament-modifying compound, a protein kinase inhibitor and/or a polypeptide growth factor, the supplement not being derived from a serum supplement of the culture medium; (iv) a method of redifferentiating dedifferentiated chondrocytes, the method comprising culturing dedifferentiated chondrocytes under culturing conditions which comprise a culture medium including at least one supplement selected from the group consisting of ascorbic acid, beta-glycerophosphate, pyruvate and IGF-I, the culturing conditions being devoid of a three dimensional support and/or of a biomolecule-coated support; (v) a method of isolating mandibular condyle chondrocytes; and (vi) an isolated mandibular condyle tissue which comprises chondrocytes and is depleted of fibroblast-like cells and/or myocytes.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The file of this patent contains at least one drawing executed in color photograph. Copies of this patent with color photograph(s) will be provided by the Patent and Trademark Office upon request and payment of necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-d are phase contrast photomicrographs depicting in-vitro differentiation of chondrocytic cells in 2-week cultures of primary chondrocytes. Mandibular condyle-derived chondrocytes (MCDC) were isolated from condyles of 3 day old ICR mice by stepwise collagenase digestion. Cells were plated at a concentration of $5 \times 10^5$ cells/mL in 6-well plates and grown in calcium-free Dulbecco's modified Eagle's medium (DMEM) supplemented with 100 micrograms/mL ascorbic acid, 10 millimolar beta-glycerophosphate, 1 millimolar calcium chloride, 1 millimolar sodium pyruvate, 10% FCS, and antibiotics. FIG. 1a depicts the cell culture after 18 hours in which cells attach to substrate and display a fibroblastoid morphology. FIG. 1b depicts the cell culture after 3 days in which the cells are subconfluent and have lost their long processes. FIG. 1c depicts the cell culture after 5 days in which the cells regain their polygonal shape. FIG. 1d depicts the cell culture after 2 weeks in which the cells cluster to form cartilaginous nodules (arrows). FIGS. 1a-c and 1d were photographed at ×190 and ×95 original magnification, respectively.

Figure 2A:
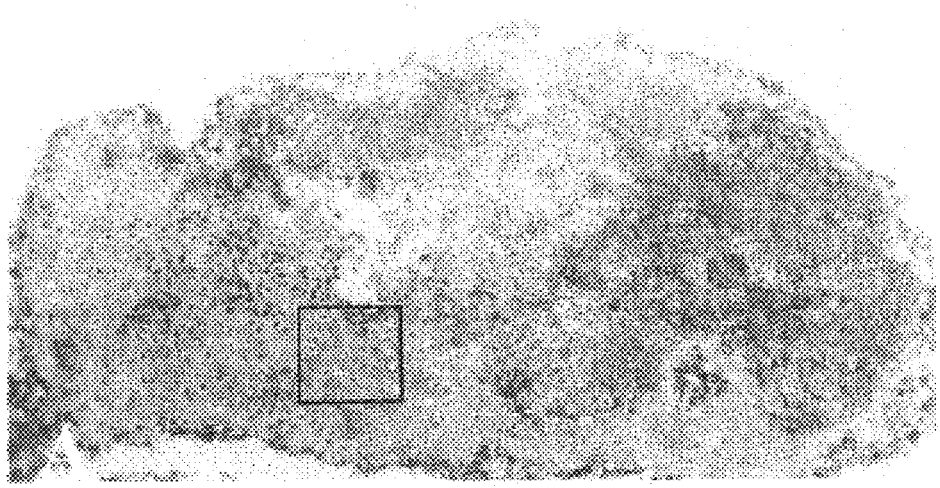
Figure 2B:
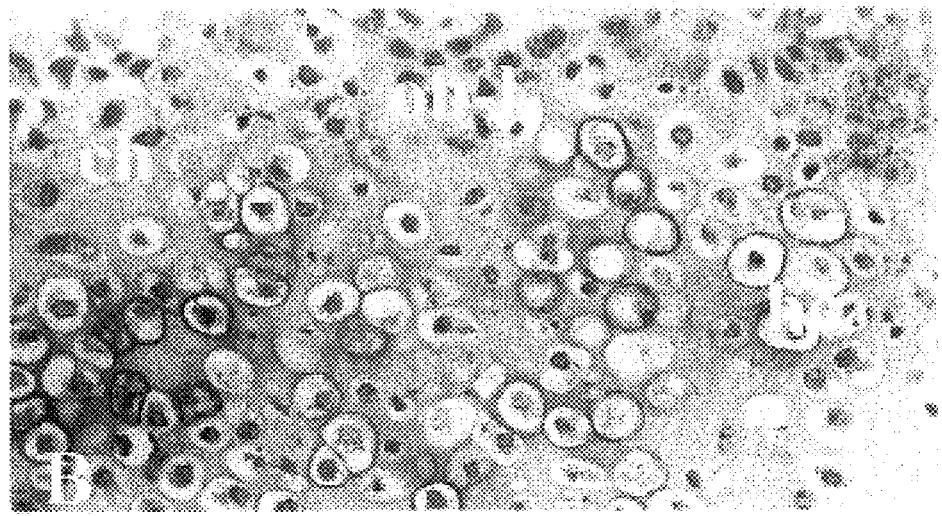

FIGS. 2a-b are photomicrographs depicting the capacity of the late primary chondrocyte cultures to display morphological changes typical of the endochondral ossification cascade. Shown is the histological appearance of a 3-week old cartilaginous nodule spontaneously formed in MCDC culture derived from chondrocytes. Nodules formed after 3 weeks were routinely processed for paraffin embedding and sections were stained with acidic (pH 2.5) alcian blue and hematoxylin and eosin (H&E). FIG. 2a depicts the heterogeneity of the nodular cell composition at an original magnification of ×190. FIG. 2b depicts nodular chondrocytes (ch), hypertrophic cells (hc), and osteoblast-like cells (ob-1). The field shown in FIG. 2b corresponds to an enlargement (original magnification ×240) of the area delimited in FIG. 2a.

Figure 3A:
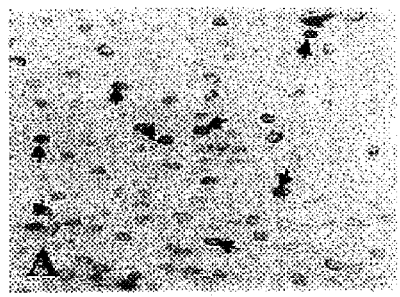
Figure 3B:
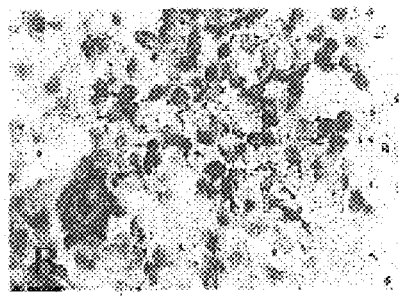
Figure 3C:
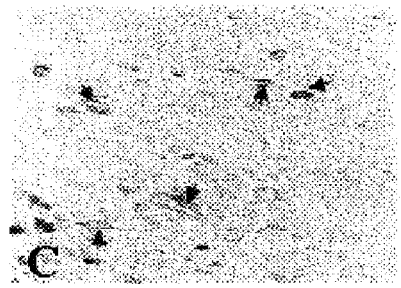
Figure 3D:
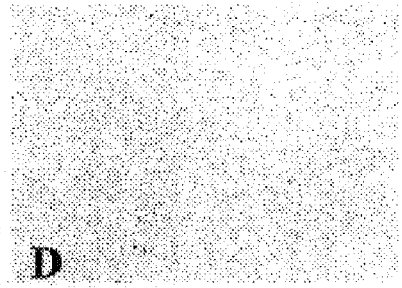
Figure 3E:
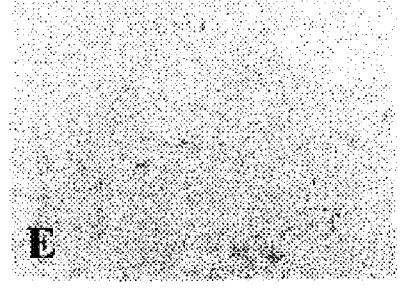
Figure 3F:
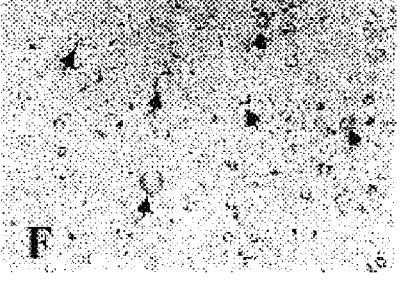
Figure 3G:
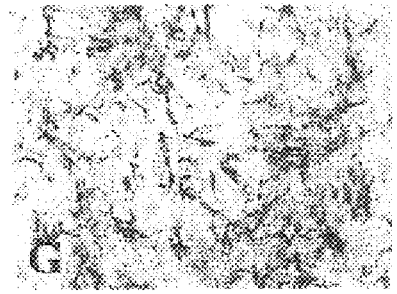
Figure 3H:
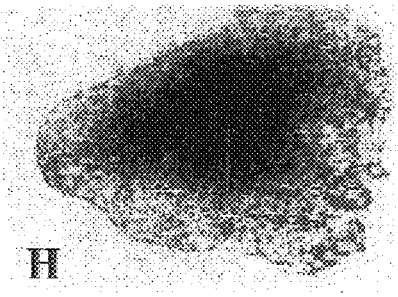

FIGS. 3a-h are photomicrographs depicting expression of chondrocyte development specific genes throughout 14 days of MCDC culture. Condylar chondrocytes were separated and plated under the same conditions described in FIG. 1. Cultures incubated for 1, 3, 5, and 14 days were fixed with paraformaldehyde, permeabilized with Triton X-100, and immunostained with antibody specific for one of the following: proliferating cell nuclear antigen (PCNA), IGF-I receptor, and type I, type II, or type X collagen. One day old cultures positively stain for PCNA (FIG. 3a, arrows) and IGF-I receptor (FIG. 3b). Three day old cultures positively stain for type I collagen (FIG. 3c, arrows) but negatively for type II collagen (FIG. 3d). On day 7, cells negatively stain for type I collagen (FIG. 3e) and positively stain for type II collagen (FIG. 3f, arrows). After 14 days of incubation, cells secrete type II collagen into the intercellular space (FIG. 3g) and nodular cells produce type X collagen (FIG. 3h). Magnification FIGS. 3a-g, ×90; FIG. 3h, ×95.

Figure 4:
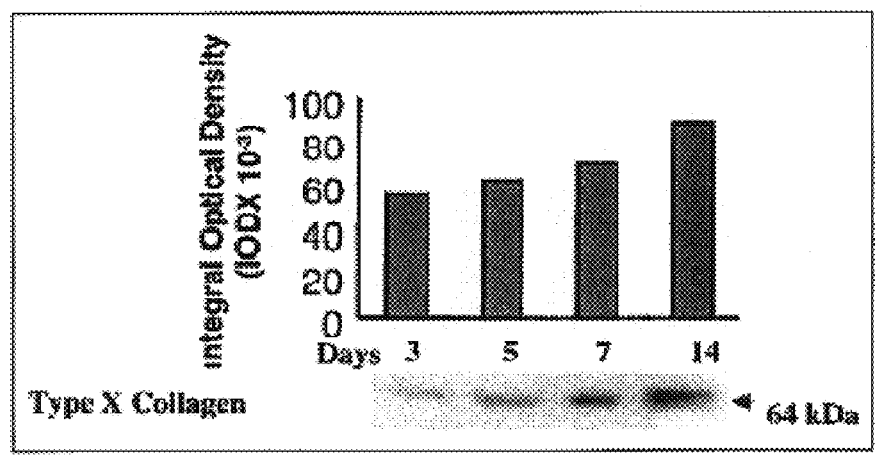

FIG. 4 is a bar graph/Western blot combination diagram depicting increases in expression of type X collagen protein during MCDC culture. Quantification of the changes in the levels of type X collagen produced throughout the culture was performed by immunoblotting analysis of lysates derived from 3, 5, 7, and 14 day old cultures. Cell lysates, prepared from pools of two or three confluent 35-mm plates, 25 micrograms lysate protein per lane, were separated by reducing SDS-PAGE and electrotransferred to nitrocellulose membrane. Blots were incubated with mouse anti type X collagen antibody (clone X-AC9, MS-852-P, NeoMarkers) and type X collagen was quantitated via densitometry.

Figure 5:
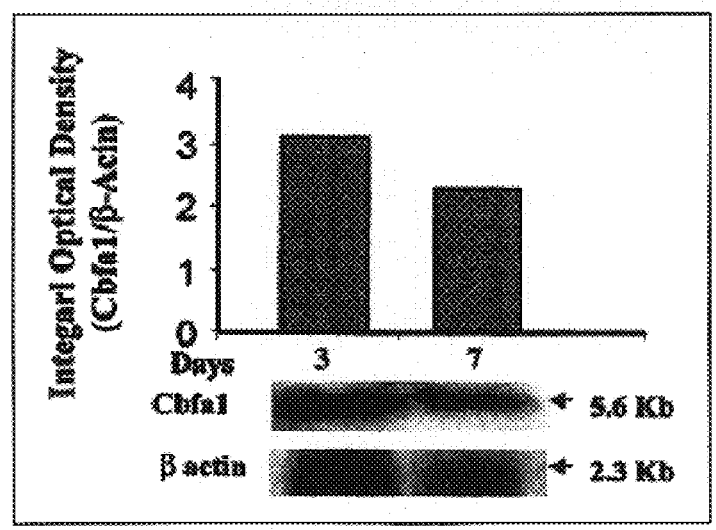

FIG. 5 is a bar graph/RNA hybridization blot combination diagram depicting expression of high levels of core-binding factor alpha1 (Cbfa1) mRNA expression in 3 day MCDC cultures decreasing by 35% in 7 day cultures. RNA samples extracted from pools of 3 and 7 day old cultures were separated via agarose gel electrophoresis and transferred to a nylon membrane. Cbfa1 transcript was detected by hybridization using $^{32}$P-labeled 633-bp fragment of the Cbfa1 coding region. For sample normalization, levels of beta-actin in the samples were also analyzed. Expression levels were analyzed via densitometry and normalized to beta-actin levels.

FIGS. 6a-d are photomicrographs depicting chondrogenesis specific decreases in levels of Cbfa1 mRNA expression in cultured MCDCs. FIG. 6a shows that cells of 3 day old cultures already express Cbfa1 (arrows). Levels of Cbfa1 are increased in the 5 day old culture (FIG. 6b, arrows) and have dropped markedly on day 7 (FIG. 6c). Negative control hybridization with the digoxigenin-labeled sense RNA probe (SEQ ID NO: 5) was negative (FIG. 6d). Original magnification: ×240.

Figure 7A:
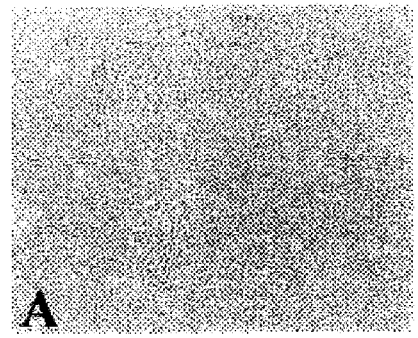
Figure 7B:
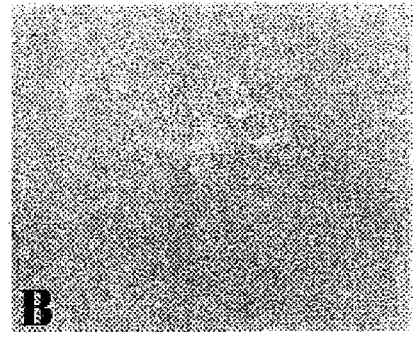
Figure 7C:
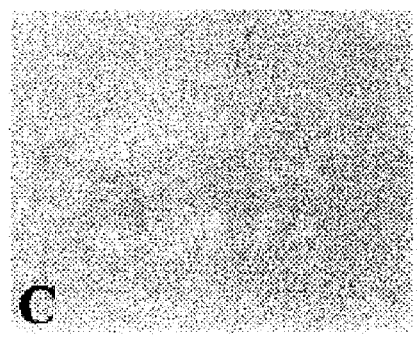
Figure 7D:
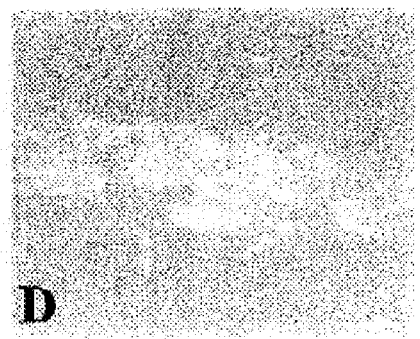
Figure 7E:
Figure 7F:

FIGS. 7a-f are photomicrographs depicting stimulation of chondrogenesis in cultured MCDCs by IGF-I. Chondrocytes released from mandibular condyles were cultured in the presence or absence of $10^{-7}$ molar IGF-I for 3 days (FIGS. 7a-b) 7 days (FIGS. 7c-d) and 14 days (FIGS. 7e-f). At all stages, IGF-I treated culture (FIGS. 7b, 7d and 7f) seems to be more developed than corresponding untreated controls (FIGS. 7a, 7c and 7e, respectively). In the 3 day old IGF-I treated culture, cells clustered, forming a primary cartilaginous nodule that under control conditions appeared only after 7 days. After 2 weeks of IGF-I treatment, well-developed cartilaginous nodules occupied most of the culture. Original magnification: ×95.

FIGS. 8a-c are photomicrographs depicting early chondrogenesis specific stimulation of Cbfa-1 expression in early MCDC cultures by IGF-I. MCDC cultures incubated for 48 hours in the presence of $10^{-8}$ molar IGF-I (FIG. 8b) express higher levels of Cbfa1 (arrows) than 2 day old untreated cultures (FIG. 8a). Culture in the presence of $10^{-7}$ molar IGF-I increases the expression of Cbfa1 even further (FIG. 8c). Original magnification: ×190.

Figure 9:

FIG. 9 is a fluorescence photomicrograph depicting green fluorescent protein (GFP) positive MCDCs genetically transformed with pcDNAI-OPG-IRES-GFP. Similar results were obtained when transfecting MCDCs with pcDNAI-GLUT4-GFP (not shown).

DESCRIPTION OF THE PREFERRED EMBODIMENTS

The present invention is of methods of generating cultured chondrocytes/bone cells, methods of treating a cartilage/bone disease, cell cultures comprising isolated chondrocytes capable of generating endochondral bone cells when cultured, methods of redifferentiating dedifferentiated chondrocytes, isolated mandibular condyle tissues, and methods of isolating mandibular condyle chondrocytes. Specifically, the present invention relates to methods of isolating and culturing mandibular condyle chondrocytes so as to generate cultured chondrocytes/endochondral bone cells therefrom under culturing conditions devoid of a three dimensional support and/ or of a biomolecule coated support, and which employ a culture medium devoid of a microfilament-modifying compound supplement, a protein kinase inhibitor supplement, and/or a polypeptide growth factor supplement, where such a supplement is not derived from a serum supplement of the culture medium. By virtue of enabling generation of cultured chondrocytes/bone in the absence of such supports and of such culture medium supplements, the method of the present invention is optimal for generating cultured chondrocytes/ endochondral bone cells having utility for treating cartilage/ bone diseases, for testing cartilage/bone disease drugs/treatment methods in-vitro, and for modeling processes of normal and pathogenic growth and differentiation of cartilage and bone in-vitro.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

As described hereinabove, optimal therapeutic options are lacking for numerous bone and cartilage diseases. Such diseases include highly debilitating diseases, such as arthritis, having enormous medical and economic impact. An optimal strategy for treating such diseases would be via therapeutic administration of cultured chondrocytes/bone cells/tissues to replace lost/damaged cartilage/bone.

Various methods of generating cultured chondrocytes/ bone cells in-vitro have been described by the prior art.

Such approaches include culturing limb mesenchyme in micromass cultures in three-dimensional collagen and agarose gels; isolated cells of mouse limb bud mesenchyme, or dedifferentiated human articular chondrocytes in alginate beads; rabbit growth plate chondrocytes in soft agar, or on a substrate coated with type I collagen, type II collagen or fibronectin; primary chondrocytes in the presence of fibroblast growth factor (FGF)-2 in three-dimensional polymer scaffolds; dedifferentiated rabbit articular chondrocytes in the presence of transforming growth factor (TGF)-beta 1, with and without the microfilament modifying drug dihydrocytochalasin B; in the presence of the protein kinase C (PKC)/ actin polymerization antagonist staurosporine primary chondrocytes, chick embryo wing bud mesenchyme micromass, or fibroblasts under hypoxic conditions; and mesenchymal progenitor cells using chemically defined components.

All of the aforementioned approaches, however, suffer from significant disadvantages, including incapacity to generate optimally differentiated cartilage/bone cells/tissue, incapacity to generate cultures of cartilage/bone cells/tissue of optimally long duration, and/or being excessively complex, cumbersome and/or expensive to practice.

Thus, the prior art fails to provide an optimal method of generating cultured cartilage/bone cells/tissue.

While reducing the present invention to practice mandibular condyle chondrocytes were optimally isolated, and culturing of such chondrocytes was used to generate optimally differentiated cultured chondrocytes/bone using unique and optimal culturing conditions which are devoid of a three-dimensional and a biomolecule-coated support, and which include a culture medium devoid of a supplement such as a polypeptide growth factor, a protein kinase inhibitor and a microfilament-modifying compound where such supplement is not derived from a serum supplement of the culture medium.

Thus, the present method of generating cultured chondrocytes/bone traverses many of the limitations of the prior art.

Thus, the method of the present invention can be used to optimally generate cultured chondrocytes/bone having utility for treating cartilage/bone diseases, for testing cartilage/bone disease drugs/treatment methods in-vitro, and for modeling processes of normal and pathogenic growth and differentiation of cartilage and bone in-vitro Thus, according to one aspect of the present invention there is provided a method of generating cultured chondrocytes/ endochondral bone cells. The method is effected by isolating chondrocytes from mandibular condyle tissue, and culturing the isolated chondrocytes under conditions suitable for generating cultured chondrocytes/endochondral bone cells.

As described hereinbelow, the method can be used to optimally generate cultured chondrocytes/endochondral bone cells (hereinafter cultured cells) which can be used for treating cartilage/bone diseases.

While isolating the chondrocytes from mandibular condyle tissue (hereinafter condyle tissue) may be performed in various ways, depending on the application and purpose, such isolation is preferably effected by selectively removing fibroblast-like cells and/or myocytes from the condyle tissue to thereby generate condyle tissue which is depleted of the fibroblast-like cells and/or the myocytes and which includes chondrocytes (hereinafter modified condyle tissue). Chondrocytes are then selectively harvested from the modified condyle tissue.

Further description of such an isolation approach is provided in Example 1 of the Examples section below.

As used herein, the phrase "fibroblast-like cells", refers to cells displaying extended fibroblast-like cellular processes typical of fibroblasts, fibroblasts and fibroblastoid cells.

Selectively removing fibroblast-like cells and/or myocytes from the condyle tissue may be effected in various ways, depending on the application and purpose. Preferably, such removal involves maximally removing fibroblast-like cells and myocytes from the condyle tissue. Preferably, such removal is effected in such a way as to subsequently enable selective harvesting of chondrocytes from the modified condyle tissue with minimal, more preferably without, contamination with fibroblast-like cells and myocytes. Thus, removal of fibroblast-like cells and myocytes is effected under conditions which ensure that most if not all such cells are removed while most if not all chondrocytes remain viable.

Selective removal of fibroblast-like cells and myocytes from the condyle tissue may be effected in various ways depending on the application and purpose. Preferably, such removal is effected by incubating the condyle tissue with a protease.

While any of various proteases, alone or in combination, may be employed for selectively removing the fibroblast-like cells and/or myocytes from the condyle tissue, the protease used for this purpose is preferably collagenase, more preferably type II collagenase.

Alternately, other proteases which may be employed for this purpose include dispase and trypsin.

Any one of various incubation conditions may be employed for selectively removing the fibroblast-like cells and/or myocytes from the condyle tissue with a protease. Preferably incubation is performed according to the protocol set forth in Example 1 of the Examples section which follows.

As is described in Example 1 of the Examples section below, incubating the condyle tissue with type II collagenase according to the protocol set forth therein can be used for selectively removing fibroblast-like cells and myocytes therefrom.

As mentioned hereinabove, following selective removal of fibroblast-like cells and/or myocytes from the condyle tissue, the chondrocytes are preferably selectively harvested from the modified condyle tissue.

Preferably, the step of incubating the isolated condyle tissue with a protease so as to selectively release chondrocytes from the isolated condyle tissue includes isolating the chondrocytes released from the isolated condyle tissue (hereinafter released chondrocytes).

Preferably, prior to harvesting the chondrocytes from the modified condyle tissue, the modified condyle tissue is isolated in order to enable harvesting of the chondrocytes with minimal, or more preferably without, contamination with fibroblast-like cells/myocytes selectively removed therefrom in the previous step.

Isolating the modified condyle tissue is preferably performed in such a way as to isolate the modified condyle tissue from the fibroblast-like cells and myocytes removed therefrom in the preceding protease treatment step, more preferably in such a way as to maximally isolate, more preferably completely isolate, the modified condyle tissue from cells/particles released therefrom during the preceding protease treatment step.

Any of various methods may be employed for isolating the modified condyle tissue. Such isolation may be conveniently performed as described in Example 1 of the Examples section below, namely by allowing a suspension containing the modified condyles and released fibroblast-like cells and myocytes to stand for 2-3 minutes so as to allow selective sedimentation of modified condyle tissue. The supernatant which contains most of the released fibroblast-like cells and myocytes is then removed from the sedimented modified condyle tissue. Optionally, in order to optimally isolate the modified condyle tissue from the released fibroblast-like cells and myocytes, the sedimented modified condyle tissue can be resuspended in a liquid medium, allowed to sediment as described above, and the supernatant, which contains residual released fibroblast-like cells and myocytes is removed therefrom.

As is illustrated and described in Example 1 of the Examples section below, the present invention can be used to isolate a modified condyle tissue of the present invention according to the protocol set forth therein.

Hence, the present invention provides an isolated mandibular condyle tissue which comprises chondrocytes and is depleted of fibroblast-like cells and/or myocytes.

While any of various proteases, alone or in combination, may be utilized for selectively releasing chondrocytes from the isolated condyle tissue the protease employed for this purpose is preferably collagenase, more preferably type II collagenase.

Alternately, other proteases which may be employed for this purpose include dispase and trypsin.

Preferably, the same protease(s) is/are employed for selectively removing fibroblast-like cells and/or myocytes from the condyle tissue and for selectively releasing chondrocytes from the modified condyle tissue.

While any of various incubation conditions may be employed for selectively releasing chondrocytes from the isolated condyle tissue using a protease, such incubation is preferably performed according to the protocol set forth in Example 1 of the Examples section below.

According to the teachings of the present invention, incubating the modified condyle tissue with the protease may be performed a predetermined number of times, as appropriate, in order to obtain a desired cell fraction, such as an optimally homogeneous chondrocyte fraction.

Preferably, following each incubation of the modified condyle tissue with the protease, the cells released are harvested so as to obtain separate fractions, each of which containing a distinct cell population.

To obtain an optimally homogeneous chondrocyte fraction, the modified condyle tissue is preferably incubated with a protease once.

To obtain a cell fraction significantly enriched for hypertrophic cells, the modified condyle tissue is preferably incubated with a protease twice.

The composition of the cell fraction released following each incubation with a protease may be advantageously monitored so as to identify a cell fraction having a desired cellular composition, such as a suitably and/or optimally pure chondrocyte fraction.

Analysis of the cellular content, such as the chondrocyte content, of a cell fraction may be performed using any of various techniques well known to the ordinarily skilled artisan. Such analysis may be conveniently performed according to techniques described and illustrated in Example 1 of the Examples section below. These techniques include: visual microscopic examination for chondrocyte specific morphological characteristics which include refractive cell margins (visible via phase-contrast microscopy) and a polygonal cell shape. Such chondrocyte specific morphological characteristics are clearly distinguishable by one of ordinary skill in the art from those of fibroblast-like cells and myocytes which have typical adhesion processes and an elongated fibrillar appearance, respectively. Suitable techniques for identifying/characterizing chondrocytes further include detection of expression/display of chondrocyte specific genes/gene products, such as, for example: immunohistochemical detection of insulin like growth factor (IGF)-I receptor, type I collagen or type II collagen; or detection of mRNA encoding core-binding factor alpha1 (Cbfa1) via RNA blot hybridization.

As is described and illustrated in Example 1 of the Examples section below, immunohistochemical detection of insulin like growth factor (IGF)-I receptor or type II collagen, or detection of mRNA encoding core-binding factor alpha1 (Cbfa1) via RNA blot hybridization according to the protocol set forth in Example 1 of the Examples section which follows can be used for detecting and characterizing chondrocytes.

As is described and illustrated in Example 1 of the Examples section below, a homogeneous population of chondrocytes is released after incubating the modified condyle tissue with a protease once according to the protocol set forth in Example 1 of the Examples section below.

As is also described and illustrated in Example 1 of the Examples section below, a cell fraction enriched for hypertrophic cells is released after incubating the modified condyle tissue with a protease twice according to the protocol set forth in Example 1 of the Examples section below.

As mentioned hereinabove, the step of incubating the isolated condyle tissue with a protease so as to selectively release chondrocytes therefrom preferably includes isolating the released chondrocytes. Preferably, such isolation is performed as soon as possible, more preferably immediately, following release of the chondrocytes from the modified condyle tissue.

Isolating the released chondrocytes may be performed using any of various techniques. Preferably, such isolation is performed as described in Example 1 of the Examples section below, namely by allowing a suspension containing the modified condyle tissue and chondrocytes released therefrom to stand for 2-3 minutes so as to allow selective sedimentation of the condyles. The supernatant which contains most of the released chondrocytes is then harvested and the chondrocytes are isolated therefrom by centrifugation. Preferably, the pelleted chondrocytes are promptly resuspended in culture medium following centrifugation thereof in order to effectively terminate proteolysis by the protease used for removal thereof from the isolated condyle tissue.

While not being bound to a paradigm, the present inventors are of the opinion that prompt isolation of the released chondrocytes optimally enables the subsequent generation therewith of the cultured cells of the present invention by virtue of minimizing proteolytic damage thereto by the protease used to facilitate their release.

As is described and illustrated in Example 1 of the Examples section below, the present invention can be used for isolating chondrocytes from isolated mandibular condyle tissue of the present invention.

Hence, the present invention provides a method of isolating chondrocytes from mandibular condyle tissue.

The method of the present invention of isolating chondrocytes from mandibular condyle tissue is unique relative to the prior art, enabling for the first time culturing of mandibular condyle derived chondrocytes, which in turn enables generation of the cultured cells of the present invention, as described hereinbelow.

As mentioned hereinabove, following isolation thereof the isolated chondrocytes are cultured under conditions suitable for generating the cultured cells of the present invention.

According to the teachings of the present invention, depending on the application and purpose, culturing the isolated chondrocytes so as to generate the cultured cells of the present invention may be effected using culturing conditions which include: (i) any of various supports; (ii) culturing the isolated chondrocytes at any of various levels of confluence; (iii) any of various culture media; (iv) any of various oxygenation levels; (v) culturing the isolated chondrocytes for any of various durations; (vi) passaging the isolated chondrocytes any of various predetermined minimum number of times; and/or (vii) culturing chondrocytes derived from an organism at any of various stages of differentiation.

As mentioned hereinabove, culturing the isolated chondrocytes may be effected so as to generate the cultured cells of the present invention using culturing conditions which, depending on the application and purpose, include any of various supports.

Preferably, the culturing conditions are devoid of a three dimensional support or of a biomolecule-coated support, more preferably of a three dimensional support and of a biomolecule coated support.

Culturing the isolated chondrocytes may be performed using culturing conditions devoid of any three dimensional support whatsoever, including a three dimensional such as a bead matrix, a gel, a polymer scaffold or a semi-solid substance. Furthermore, culturing the isolated chondrocytes may be performed using culturing conditions devoid of a support coated with any biomolecule whatsoever, including a biomolecule such as a polypeptide, an extracellular matrix component, collagen, type I collagen, type II collagen and fibronectin.

As mentioned hereinabove, culturing the isolated chondrocytes so as to generate the cultured cells of the present invention may be effected using culture conditions including, depending on the application and purpose, any of various culture media.

Culturing the isolated chondrocytes so as to generate the cultured cells of the present invention is preferably effected using the culture medium described in Example 1 of the Examples section below.

Culturing the isolated chondrocytes so as to generate the cultured cells of the present invention may be advantageously effected using a culture medium devoid of a supplement such as a microfilament-modifying compound, a protein kinase inhibitor, and/or a polypeptide growth factor, where such a supplement is not derived from a serum supplement of the culture medium. In particular culturing the isolated chondrocytes so as to generate the cultured cells of the present invention may be advantageously effected using a culture medium devoid of a microfilament-modifying compound supplement, a protein kinase inhibitor supplement, and/or a polypeptide growth factor supplement, where such supplement is not derived from a serum supplement of the culture medium.

As used herein, the phrase "serum supplement", refers to an animal serum supplement, such as a fetal serum or a bovine serum supplement, added to a culture medium.

In particular, culturing the isolated chondrocytes so as to generate the cultured cells of the present invention may be effected using a culture medium devoid of any non-serum supplement derived microfilament modifying compound supplement, including dihydrocytochalasin B, staurosporine, and/or an actin filament-modifying compound.

In particular, culturing the isolated chondrocytes so as to generate the cultured cells of the present invention may be effected using a culture medium devoid of any non-serum supplement derived protein kinase inhibitor supplement, including staurosporine and/or a PKC inhibitor.

In particular, culturing the isolated chondrocytes so as to generate the cultured cells of the present invention may be effected using a culture medium devoid of any non-serum supplement derived polypeptide growth factor supplement, including a transforming growth factor (TGF) such as TGF-beta1, a fibroblast growth factor (FGF) such as FGF-2, and/or an insulin like growth factor (IGF) such as IGF-I.

Culturing the isolated chondrocytes so as to generate the cultured cells of the present invention is preferably effected using culturing conditions which comprise a culture medium including at least one, more preferably two, more preferably all three of: an ascorbic acid supplement, a beta-glycerophosphate supplement, and a pyruvate supplement.

The pyruvate supplement is preferably derived from a sodium pyruvate supplement.

The concentration of the ascorbic acid supplement in the culture medium is preferably selected from the range of 10 micrograms/mL to 1 milligram/mL, more preferably the concentration of the ascorbic acid supplement in the culture medium is about 100 micrograms/mL, and most preferably the concentration of the ascorbic acid supplement in the culture medium is 100 micrograms/mL.

As used herein the term "about" refers to plus or minus 10%.

Preferably, the concentration of the beta-glycerophosphate supplement in the culture medium is selected from the range of 1-100 millimolar, more preferably the concentration of the beta-glycerophosphate supplement in the culture medium is about 10 millimolar, and most preferably the concentration of the beta-glycerophosphate supplement in the culture medium is 10 millimolar.

The concentration of pyruvate supplement in the culture medium is preferably selected from the range of 100 nanomolar to 10 millimolar, more preferably the concentration of the pyruvate supplement in the culture medium is about 1 millimolar, and most preferably the concentration of the pyruvate supplement in the culture medium is 1 millimolar.

Preferably, culturing the isolated chondrocytes so as to generate the cultured cells of the present invention is effected using culturing conditions which comprise a culture medium including an IGF-I supplement.

The concentration of IGF-I supplement in the culture medium is preferably selected from the range of 1 nanomolar to 1 micromolar, more preferably the concentration of the IGF-I supplement in the culture medium is about 10 nanomolar, and most preferably the concentration of the IGF-I supplement in the culture medium is about 100 nanomolar.

As mentioned hereinabove, culturing the isolated chondrocytes so as to generate the cultured cells of the present invention may be effected using culturing conditions which, depending on the application and purpose, are characterized by any of various oxygenation levels.

Culturing the isolated chondrocytes so as to generate the cultured cells of the present invention may be effected, depending on the application and purpose, using hypoxic culturing conditions, more preferably, normoxic culturing conditions.

As mentioned hereinabove, culturing the isolated chondrocytes so as to generate the cultured cells of the present invention may be effected using culturing conditions which, depending on the application and purpose, include culturing the isolated chondrocytes at any of various levels of confluence.

Preferably, the culturing conditions include culturing a confluent population of the isolated chondrocytes, more preferably a subconfluent population of the isolated chondrocytes.

As is described in Example 1 of the Examples section below, culturing the isolated chondrocytes under culturing conditions which: (i) include a culture medium devoid of a microfilament-modifying compound supplement, a protein kinase inhibitor supplement, and a polypeptide growth factor supplement, where such supplements are not derived from a serum supplement of the culture medium; (ii) are devoid of a three dimensional and of a biomolecule coated support; (iii) are normoxic; and (vi) include culturing a subconfluent population of isolated chondrocytes, can be used to generate the cultured cells of the present invention. Such capacity of the present invention to enable generation of the cultured cells of the present invention under such culturing conditions is unique relative to the prior art, and thereby overcomes numerous limitations of the prior art, as described hereinabove.

As mentioned hereinabove, culturing the isolated chondrocytes so as to generate the cultured cells of the present invention may be effected using culturing conditions which, depending on the application and purpose, include culturing the isolated chondrocytes for any of various durations, and/or include passaging the cultured chondrocytes any of various predetermined minimum number of times.

In cases where the isolated chondrocytes initially undergo dedifferentiation following culturing thereof, which will generally be the case when culturing isolated chondrocytes according to the teachings of the present invention, as described in Example 1 of the Examples section below, the isolated chondrocytes are preferably cultured for a duration sufficient for these to display a desired level of chondrocytic redifferentiation. As is described and illustrated in Example 1 of the Examples section below, dedifferentiation of cultured chondrocytes will typically be manifested as a loss of chondrocyte specific characteristics such as polygonal cell shape, refractive cell contours, and by down-regulation of type II collagen production, and will also typically be manifested by up-regulation of production of type I collagen, and by a cell morphology characterized by fibroblast-like elongated cellular processes.

Preferably, redifferentiation of dedifferentiated chondrocytes can be facilitated by culturing such chondrocytes according to the teachings of the present invention for a minimum duration selected from a range of 1-6 days, depending on the specific stage of dedifferentiation thereof. For example, dedifferentiated chondrocytes having just reached a stage of dedifferentiation characterized by loss of polygonal cell shape, and/or characterized by fibroblast-like extended cellular processes are preferably redifferentiated by culturing such cells according to the teachings of the present invention for a duration of 4-6 days. Preferably, dedifferentiated chondrocytes having just reached a stage of dedifferentiation characterized by down-regulation of type II collagen production and by up-regulation of type I collagen are redifferentiated by culturing such cells according to the teachings of the present invention for a duration of 2-4 days.

As is described and illustrated in Example 1 of the Examples section below, culturing dedifferentiated chondrocytes having just reached a stage of dedifferentiation characterized by loss of polygonal cell shape and characterized by fibroblast-like extended cellular processes for a duration of 4-6 days according to the teachings of the present invention can be used to redifferentiate such cells.

As is described and illustrated in Example 1 of the Examples section below, culturing dedifferentiated chondrocytes having just reached a stage of dedifferentiation characterized by down-regulation of type II collagen production and by up-regulation of type I collagen for a duration of 2-4 days according to the teachings of the present invention can be used to redifferentiate such cells.

Hence, the present invention provides a method of redifferentiating dedifferentiated chondrocytes.

It will be appreciated by the ordinarily skilled artisan that by virtue of the essential universality of the stimuli required for inducing chondrocytic differentiation of dedifferentiated chondrocytes, regardless of their source, that the method of redifferentiating dedifferentiated chondrocytes of the present invention can be used for redifferentiating dedifferentiated chondrocytes derived from essentially any source. In particular, since as described in Example 1 of the Examples section below, the method of redifferentiating dedifferentiated chondrocytes of the present invention can be used for redifferentiating mammalian condylar chondrocytes, the method of redifferentiating dedifferentiated chondrocytes of the present invention is suitable for redifferentiating dedifferentiated chondrocytes derived from essentially any type of condyle and from essentially any mammal, including from a human condyle.

In general isolated chondrocytes will undergo dedifferentiation and redifferentiation when cultured according to the teachings of the present invention for a duration of 5-7 days, for example as described and illustrated in Example 1 of the Examples section below.

As is further illustrated and described in Example 1 of the Examples section which follows, culturing isolated chondrocytes according to the teachings of the present invention for predetermined durations can be used to generate cultured cells of the present invention displaying various levels of chondrocyte/endochondral bone cell specific differentiation as a function of culture duration. Hence, it will be advantageous to monitor a culture of the present invention with maximal frequency, preferably at least daily, so as to obtain cultured cells of the present invention having desired characteristics.

For generating cultured chondrocytes, the isolated chondrocytes are preferably cultured according to the teachings of the present invention for a duration selected from a range of 5-21 days. As is shown and explained in Example 1 of the Examples section below, culturing isolated chondrocytes according to the teachings of the present invention for a duration of 5-21 days can be used to generate the cultured chondrocytes of the present invention.

In order to generate cultured endochondral bone cells characterized by endochondral bone nodule formation, high levels of secretion of type II collagen into the intercellular space, production of type X collagen, differentiation of chondroblasts, differentiation of mature chondrocytes, differentiation of osteoblasts, and/or differentiation of hypertrophic cells, the isolated chondrocytes are preferably cultured according to the teachings of the present invention for a minimum duration selected from a range of 14-21 days, depending on the desired level of endochondral bone cell differentiation. Preferably, the greater the level of endochondral bone cell differentiation desired, the greater the culture duration.

As is illustrated and described in Example 1 of the Examples section below, culturing isolated chondrocytes according to the teachings of the present invention for 14-21 days can be used for generating endochondral bone cells characterized by high levels of secretion of type II collagen into the intercellular space, production of type X collagen, and differentiation of chondroblasts, mature chondrocytes, osteoblasts, and hypertrophic cells.

Hence, the present invention provides a cell culture comprising isolated chondrocytes capable of generating endochondral bone cells when cultured according to the teachings of the present invention.

It will be appreciated by the ordinarily skilled artisan that by virtue of the essential universality of the stimuli required for inducing endochondral bone cell specific differentiation of chondrocytes regardless of their source, that the present invention provides a cell culture comprising isolated chondrocytes derived from essentially any source. In particular, since as described in Example 1 of the Examples section below, the present invention provides a cell culture comprising isolated chondrocytes capable of generating endochondral bone cells when cultured according to the teachings of the present invention where such chondrocytes are derived from a mammalian condyle, the present invention provides a cell culture comprising isolated chondrocytes capable of generating endochondral bone cells when cultured according to the teachings of the present invention where such chondrocytes are derived from a human condyle.

In order to generate long term cultured chondrocytes having lost the capacity to generate endochondral bone nodules, the isolated chondrocytes are preferably cultured under culturing conditions including passaging the isolated chondrocytes at least four times, more preferably at least five times. As is shown and described in Example 1 of the Examples section which follows, culturing the isolated chondrocytes under culturing conditions including passaging the isolated chondrocytes four or five times can be used for generating long term cultured chondrocytes having lost the capacity to generate endochondral bone nodules.

As described hereinabove, culturing the isolated chondrocytes so as to generate the cultured cells of the present invention may be effected using culturing conditions which, depending on the application and purpose, include culturing chondrocytes from an organism at any of various stages of differentiation.

Preferably, the organism is at the earliest stage of development possible.

Preferably, the isolated chondrocytes are derived from a subadult organism, more preferably from a neonatal organism, more preferably from an organism less than a week old, more preferably from an organism 3 days old or less, and most preferably from a gestational stage organism.

As is shown in Example 1 of the Examples section which follows, culturing chondrocytes isolated from a three day old organism according to the teachings of the present invention can be employed for generating the cultured cells of the present invention.

Without being bound to a paradigm, the present inventors are of the opinion that the capacity of isolated chondrocytes derived from a subadult organism to generate the cultured cells of the present invention when cultured according to the teachings of the present invention is due to the optimal proliferative/differentiative capacity of chondrocytes isolated from an organism at such a developmental stage or earlier.

As mentioned hereinabove, the cultured cells of the present invention can be used in any of various applications.

As described in Example 1 of the Examples section below and as described hereinabove, the cultured cells of the present invention have the capacity to proliferate and to differentiate into chondrocytes/endochondral bone cells at essentially any desired stage of differentiation. By virtue of such capacities, the cultured cells of the present invention can be administered in-vivo so as to repair/replace lost/damaged cartilage/bone.

By virtue of proliferating and differentiating in-vitro into cartilage/endochondral bone displaying any of various desired characteristics, the cutured chondrocytes/endochondral bone cells of the present invention can be used for testing cartilage/bone disease drugs/treatment methods in-vitro, and for modeling processes of normal and pathogenic growth and differentiation of cartilage and endochondral bone in-vitro.

The cultured cells of the present invention can be advantageously genetically transformed to express essentially any desired exogenous polynucleotide/gene. It will be appreciated that by virtue of such capacity, the cultured cells of the present invention can be genetically transformed to express or overexpress essentially any desired polypeptide or RNA sequence. It will be further appreciated that by virtue of such capacity the cultured cells of the present invention can be genetically transformed, for example to express a suitable antisense RNA or ribozyme, so as to down-regulate expression of essentially any endogenous gene. One of ordinary skill in the art would possess the knowledge required to achieve a desired biological effect in the cultured cells of the present invention via genetic transformation thereof with an exogenous polynucleotide/gene.

Preferably, the exogenous polynucleotide/gene encodes human osteoprotegerin (OPG; GenBank Accession No. NM_002546), and/or human glucose transporter (GLUT4; GenBank Accession No. M20747).

As is described in Example 2 of the Examples section which follows, the cultured cells of the present invention can be genetically transformed with an exogenous polynucleotide to express OPG or GLUT4, respectively.

In order to express an exogenous polynucleotide/gene, the cultured cells of the present invention are preferably transformed with a nucleic acid construct capable of expressing such a polynucleotide/gene in these cell types.

To enable expression of an exogenous polynucleotide/gene in the cultured cells of the present invention, the construct includes a promoter sequence capable of directing transcription of the exogenous polynucleotide/gene in mammalian cells, preferably mammalian chondrocytes. Such a promoter can be constitutive, inducible or growth regulatable depending on the gene expressed and application. In addition, the construct may advantageously include a signal sequence for secretion of a polypeptide expressed from the exogenous polynucleotide/gene from a host cell in which it has been introduced. Preferably the signal sequence for this purpose is a mammalian signal sequence. Optionally, the construct may advantageously include a signal that directs mRNA polyadenylation and/or a translation termination sequence.

Examples of chondrocyte specific promoter sequences suitable for use in the construct include, but are not limited to, type II collagen promoter COL2A1 (for example, refer to Osaki et al., 2003. Biochem J. 369(Pt 1):103) for expression in human chondrocytes, and type X collagen promoter for expression in human hypertrophic chondrocytes (refer, for example, to Chambers et al., 2002. FEBS Lett. 531:505). Ample guidelines for selecting and employing appropriate chondrocyte specific promoters is provided in the art (for example, refer to: Madry et al., 2003. J Gene Med. 5:502-9; van der Kraan P M. et al., 2002. Osteoarthritis Cartilage 10:631-7; Meynier de Salinelles V. et al., 2002. FEBS Lett. 518:67-71; Samuel R E. et al., 2002. Hum Gene Ther. 13:791-802; Feng et al., 2003. J Biol. Chem. May 20 [Epub ahead of print]; Loeser et al., 2003. J Biol Chem. 278:24577; Martin J A, and Buckwalter J A., 2003. J Bone Joint Surg Am. 85-A Suppl 2:106; Kypriotou M. et al., 2003. DNA Cell Biol. 22:119; van Beuningen H M. et al., 2002. Osteoarthritis Cartilage 10:977).

The construct may be advantageously based on a commercially available mammalian expression vector or derivative thereof. Examples of suitable vectors include, but are not limited to, pcDNA3, pcDNA3.1(+/−), pZeoSV2(+/−), pSecTag2, pDisplay, pEF/myc/cyto, pCMV/myc/cyto, pCR3.1, which are available from Invitrogen, pCI which is available from Promega, pBK-RSV and pBK-CMV which are available from Stratagene, pTRES which is available from Clontech, and their derivatives and modificants.

Any promoter and/or regulatory sequences included in the mammalian expression vectors described above can be utilized to direct the transcription of an exogenous polynucleotide/gene. However, since such vectors are readily amenable to sequence modifications via standard recombinant techniques, additional regulatory elements, promoter and/or selection markers can easily be incorporated therein if needed.

The construct can be introduced into a cell, population of cells, or tissue via any standard in-vivo or ex-vivo mammalian transformation method using any one of a variety of known methods within the art (for general guidelines refer, for example, to: [Sambrook et al., Molecular Cloning: A Laboratory Manual, Cold Springs Harbor Laboratory, New York (1989, 1992); Ausubel et al., Current Protocols in Molecular Biology, John Wiley and Sons, Baltimore, Md. (1989); Chang et al., Somatic Gene Therapy, CRC Press, Ann Arbor, Mich. (1995); Vega et al., Gene Targeting, CRC Press, Ann Arbor Mich. (1995); Vectors: A Survey of Molecular Cloning Vectors and Their Uses, Butterworths, Boston Mass. (1988); Gilboa et al., 1986. Biotechniques 4:504-512; "Methods in Enzymology" Vol. 1-317, Academic Press; See U.S. Pat. Nos. 5,464,764 and 5,487,992 for positive-negative selection methods for inducing homologous recombination]. Methods of introducing the construct into cells include, for example, stable or transient transfection, lipofection, cationic lipid-mediated transformation, dendrimer-mediated genetic transformation, polylysine-mediated genetic transformation, electroporation, infection with recombinant viral vectors, direct DNA uptake, microparticle bombardment, and the like.

The cultured cells of the present invention may be conveniently genetically transformed as described in Example 2 of the Examples section below.

Ample guidelines for specifically genetically transforming chondrocytes is provided in the art (for example, refer to: Madry et al., 2003. J Gene Med. 5:502-9; van der Kraan P M. et al., 2002. Osteoarthritis Cartilage 10:631-7; Meynier de Salinelles V. et al., 2002. FEBS Lett. 518:67-71; Samuel R E. et al., 2002. Hum Gene Ther. 13:791-802; Feng et al., 2003. J Biol Chem. May 20 [Epub ahead of print]; Loeser et al., 2003. J Biol Chem. 278:24577; Martin J A, and Buckwalter J A., 2003. J Bone Joint Surg Am. 85-A Suppl 2:106; Kypriotou M. et al., 2003. DNA Cell Biol. 22:119; van Beuningen H M. et al., 2002. Osteoarthritis Cartilage 10:977).

Viral vectors offer several advantages including optimal efficiency of transformation, and targeting to, and propagation in, specific cell types. Viral vectors can also be modified with specific receptors or ligands to alter target specificity through specific cell receptors.

Retroviral vectors represent one class of vectors suitable for use with the present invention. Defective retroviruses are routinely used in transfer of genes into mammalian cells [for review see Miller, A. D., Blood 76: 271 (1990)]. A recombinant retrovirus including an exogenous polynucleotide/gene can be constructed using well known molecular techniques. Portions of the retroviral genome can be removed to render the retrovirus replication defective and the replication defective retrovirus can then packaged into virions, which can be used to infect target cells through the use of a helper virus and while employing standard techniques. A viral vector construct such as a retroviral vector construct includes at least one transcriptional promoter/enhancer or locus-defining element(s), or other elements that control gene expression by other means such as alternate splicing, nuclear RNA export, or post-translational modification. Protocols for producing recombinant retroviruses and for infecting cells in-vitro or in-vivo with such viruses are widely available in the literature of the art [refer, for example, to Ausubel et al., (eds), Current Protocols in Molecular Biology, Greene Publishing Associates, (1989)]. Retroviruses have been used to introduce a variety of genes into many different cell types, including neuronal cells, epithelial cells endothelial cells, lymphocytes, myoblasts, hepatocytes, bone marrow cells, and chondrocytes. For a review discussing introduction of exogenous genes/polynucleotides into chondrocytes via retroviral vectors, refer, for example, to Yamada et al., 1991. J Craniofac Genet Dev Biol. 11:350.

Another suitable viral vector may be an adenoviral vector. The adenovirus is an extensively studied and routinely used gene transfer vector. Key advantages of an adenoviral vector include relatively high transduction efficiency of dividing and quiescent cells, natural tropism to a wide range of epithelial tissues and easy production of high titers [for example, refer to Russel, W. C. [J. Gen. Virol. 81: 57-63 (2000)]. Adenoviral DNA is transported to the nucleus, but does not integrate thereinto. Adenoviral vectors used in experimental medical treatments are described by Seth et al. [Adenoviral vectors for cancer gene therapy. In: P. Seth (ed.) Adenoviruses: Basic biology to Gene Therapy, Landes, Austin, Tex., (1999) pp. 103-120]. For a review discussing introduction of exogenous genes/polynucleotides into chondrocytes using adenoviral vectors, refer, for example, to van de Loo et al., 2002. Rheum Dis Clin North Am. 28:127-49.

A further suitable viral vector includes a chimeric adenovirus/retrovirus vector which combines retroviral and adenoviral components. Such a vector may be more efficient than traditional expression vectors for transducing cells [Pan et al., Cancer Letters 184: 179-188 (2002)].

A specific example of a suitable viral vector is the adenovirus-derived vector Ad-TK. This vector expresses a herpes virus thymidine kinase (TK) gene for either positive or negative selection and includes an expression cassette for desired recombinant sequences. This vector can be used to infect cells that have an adenovirus receptor (Sandmair et al., 2000. Hum Gene Ther. 11:2197-2205).

As described hereinabove, lipid-based techniques can be used for introducing an exogenous polynucleotide/gene into a cell such as a cultured cell of the present invention. Useful lipids for lipid-mediated transfer of an exogenous polynucleotide/gene are, for example, DOTMA, DOPE, and DC-Chol [for example, refer to Tonkinson et al., Cancer Investigation, 14(1): 54-65 (1996)].

As mentioned hereinabove, the cultured cells of the present invention can be administered in-vivo so as to repair/replace lost/damaged cartilage/bone.

Thus, according to another aspect of the present invention there is provided a method of treating a cartilage/bone disease in a subject. The treatment method is effected by administering a therapeutically effective dose of the cultured cells of the present invention to the subject.

As used herein, the phrase "therapeutically effective dose" refers to an amount sufficient to effect a beneficial or desired clinical result.

As used herein, the term "treating" refers to preventing onset of the disease, alleviating, attenuating, palliating or eliminating the symptoms of a disease, slowing, reversing or arresting the progression of the disease, or curing the disease.

As used herein, the, term "disease" refers to any medical disease, disorder, condition, or syndrome, or to any undesired and/or abnormal physiological, morphological, and/or physical state or condition.

The method is preferably applied to treat the disease in a mammalian subject, preferably a human subject.

Preferably, the treatment method is effected by isolating the cultured cells of the present invention prior to administering the therapeutically effective dose thereof to the subject.

Such isolation serves the function, for example, of removing undesired culture medium components from the cultured cells of the present invention. Isolating the cultured cells of the present invention can be performed by suspending such cells in a liquid medium, centrifuging the resultant cell suspension and discarding the supernatant. The pelleted cells can then be conveniently resuspended in any desired liquid medium, preferably a medium suitable for washing and administering the cells, such as phosphate-buffered saline (PBS) solution, Hank's buffered saline solution (HBSS).

Administering the therapeutically effective dose of the cultured cells of the present invention to the patient can be effected in any of various ways, depending on the application and purpose.

The cultured cells of the present invention can be administered into various regions of the body requiring cartilage/bone repair/replacement, depending on the type of disease to be treated.

Preferably, for treating a cartilage or bone disease, administering the therapeutically effective dose of the cultured cells of the present invention to the subject is effected by administering a therapeutically effective dose of cultured chondrocytes or endochondral bone cells, respectively, to the subject.

Preferably, for treating a disease affecting both bone and cartilage, the treatment method is effected by administering a therapeutically effective dose of cultured chondrocytes and cultured endochondral bone cells to the subject.

Preferably, for treating a cartilage or disease, the treatment method is effected by administering the therapeutically effective dose of the cultured cells of the present invention to a body part of the subject having missing/damaged cartilage or bone, respectively.

When administering a dose of endochondral bone cells, these cells may be administered, depending on the application and purpose, either as a mixed cell suspension, as a cell suspension composed of specific endochondral bone cell types, and/or in the form of whole endochondral bone nodules of the present invention. An endochondral bone nodule of the present invention, or portion thereof, can be converted to a cell suspension by proteolytically digesting the nodule, for example, with a protease such as collagenase, dispase or trypsin. Digestion with collagenase may be performed by incubation with 0.1% collagenase for 15 minutes. Digestion with trypsin may be performed by incubation with 0.25% trypsin for 3 minutes.

A cell suspension composed exclusively of a specific endochondral bone cell type such as osteoblasts, hypertrophic cells, chondroblasts or mature chondrocytes can be obtained by fluorescence-activated cell sorting using antibodies specific for the markers osteocalcin, type X collagen, chondromodulin I or cartilage proteoglycans, respectively. Invasive techniques such as scrape-loading, electroporation or microinjection can be used to introduce fluorophore-conjugated detection reagents inside cells so as to enable fluorescence activated sorting of cells on the basis of intracellular markers such as these.

The dose of cultured cells of the present invention is preferably administered via transplantion and/or injection. One or several doses may be administered as appropriate to achieve a desired therapeutic and/or cosmetic effect.

One of ordinary skill in the art, such as a physician, more preferably a physician specialized in the disease, such as a rheumatologist or orthopedic surgeon, will possess the necessary knowledge to determine what would constitute an effective dose, and the optimal mode of administration thereof without undue experimentation according to the teachings of the present invention. Preferably, determination of an effective dose is based on factors individual to each subject, including, for example, weight, age, physiological status, medical history, and parameters related to the disease.

Ample guidelines for treating diseases using administration of chondrocytes/endochondral bone cells is provided in the literature of the art (for treatment of cartilage injury refer, for example to Wroble, November 2000. The Physician and Sports Medicine vol. 28 no. 11; for treatment of incontinence and vesicoureteral reflux, refer, for example, to Kershen and Atala, 1999. Urol Clin North Am. 26:81; for osteochondral transplantation, refer, for example, to Barber and Chow, 2001. Arthroscopy 17:832; for treatment of deep cartilage defects in the knee, refer, for example, to Brittberg et al., 1994. N Engl J Med. 331:889; for treatment of articular cartilage defects, refer, for example, to Brittberg et al., 1996. Clin Orthop 326:270).

Preferably, the treatment method is practiced by administering cultured cells of the present invention syngeneic with the subject. Alternately, the treatment method may practiced by administering cultured cells of the present invention non-syngeneic with the subject. Preferably, the non-syngeneic cells are allogeneic with the subject. Harvesting of mandibular condyle tissue from a human subject for generating cultured cells of the present invention syngeneic with the subject can be easily practiced by one of ordinary skill in the art skill in the art, such as a surgeon, more preferably, a surgeon specialized in maxillary surgery.

It will be recognized by the skilled practitioner that when administering non-syngeneic cells or tissues to a subject, there is routinely immune rejection of such cells or tissues by the subject. Thus, the method of the present invention preferably further comprises treating the subject with an immunosuppressive regimen, preferably prior to such administration, so as to inhibit such rejection. Immunosuppressive protocols for inhibiting allogeneic graft rejection, for example via administration of cyclosporin A, immunosuppressive antibodies, and the like are widespread and standard practice in the clinic.

The present invention further envisages administration to a human subject of cultured cells derived from an animal, such as a pig, genetically engineered to avoid rejection of a graft derived from such an animal in a human (for reviews refer for example, to: Niemann et al., 2003. Reprod Domest Anim. 38:82-9; and Prather et al., 2003. Theriogenology. 59:115).

Depending on the application and purpose, the cultured cells of the present invention may be advantageously administered to the subject at any point during any of the various culturing stages described hereinabove, as appropriate.

The optimal in-vitro longevity of the chondrocytes/endochondral bone cells of the present invention confers optimal flexibility for the timing of the administration thereof. This is particularly useful for therapy protocols which are characterized by stages of variable duration, such as, for example, attainment of optimal immunosuppression in the subject prior to allogeneic cell administration. Such optimal in-vitro longevity is also useful for generating optimal numbers of cells since it enables an optimal number of culture batches to be asynchronously produced while still being simultaneously harvestable.

As described hereinabove, the cultured cells of the present invention can be genetically modified. As such, it will be appreciated that such genetic modifications can be used to enhance the therapeutic effect resulting from administering the cultured cells. In particular, such modifications may advantageously include those enhancing therapeutic growth/ differentiation of the administered cells and/or of endogenous cartilage/bone cells.

Since the cultured cells of the present invention include various types of chondrocytes and endochondral bone cells having a potent capacity for proliferating and differentiating into cartilage/endochondral bone, the cultured cells of the present invention are optimal for integrating with supporting/ damaged tissues of the subject, and for repairing/replacing damaged/missing cartilage/bone of the subject following administration thereof to the subject. As such, the treatment method can be used to treat essentially any cartilage/bone disease amenable to treatment by repair and/or replacement, respectively, of damaged and/or missing cartilage/bone. Such diseases include, but are not limited to, arthritis, articular cartilage injury, meniscal disorders, joint infections, chondrogenesis disorders and cosmetic disorders of cartilaginous and bony structures of the body, osteoarthritis, osteoporosis, bone injury and the like.

Thus, the present invention provides methodology which can be used to generate, under uniquely optimal culturing conditions relative to the prior art, highly differentiated, proliferative, and long-lived cultured chondrocytes/endochondral bone cells and tissues having optimal utility for treating cartilage/bone diseases, for testing cartilage/bone disease drugs/treatment methods in-vitro, and for modeling processes of normal and pathogenic growth and differentiation of cartilage and bone in-vitro.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual"

CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Method of Optimally Isolating Mandibular Condyle Chondrocytes, and of Culturing Primary Chondrocytes to Optimally Generate Optimally Differentiated Cultured Chondrocytes/Endochondral Bone Cells Background: Cartilage/bone diseases include numerous highly debilitating diseases, such as arthritis, which are of tremendous medical and economic impact and for which no optimal treatment methods exist. An optimal strategy for treating such diseases would be to generate and administer cultured chondrocytes/endochondral bone cells so as to replace/repair lost/damaged cartilage/bone. While various methods of generating cultured chondrocytes/bone have been proposed in the prior art, these have been highly suboptimal for various reasons, as described in the Field and Background of the Invention section above. Notably, primary chondrocyte-derived cell cultures tend to undergo dedifferentiation, acquire fibroblastic features, and lose most of the characteristics of mature chondrocytes, and the approaches which have attempted to overcome such drawbacks have proven to be suboptimally complex, cumbersome, or effective. While reducing the present invention to practice, a method of optimally generating cultured chondrocytes/endochondral bone cells was unexpectedly identified, thereby overcoming the limitations of the prior art, as described below.

Materials and Methods:

Removal of non-chondrocyte cells from condyles: Mandibular condyles derived from 3 day old ICR mice were harvested aseptically, freed of any soft tissue and cut at the mineralization front of the condyle, washed in cold Hank's buffered saline solution (HBSS), and subjected to graduated enzymatic separation. Pools of 20 condyles were incubated in 2 mL of 0.1% collagenase type II (Sigma, St. Louis, Mo.) in complete Dulbecco's modified Eagle's medium (DMEM; see below) supplemented with 2% fetal calf serum (FCS), for 30-45 minutes at 37 degrees centigrade with vigorous shaking. Cells removed from the condyles in this first digestion phase are mainly myocytes and fibroblast-like cells that had not been removed mechanically, thus leaving the condyle free of all soft tissues. To isolate the condyles from the released cells, test tubes containing the partially digested condyles were left standing for 2-3 minutes to allow selective sedimentation of the condyles and the supernatant-containing the released cell suspension was removed.

Harvesting of chondrocytes from condyles: Condyles from which fibroblast-like cells and myocytes were proteolytically removed were subjected to a second and a third collagenase digestion under the same conditions, except for a longer incubation period of 75 minutes, to yield a homogeneous cell fraction of chondrocytes. This gradual enzymatic separation of chondrocytes is specifically suitable for obtaining chondrocytes from the mandibular condyle due to the morphological structure of the latter being an apical pure cartilaginous process covered by soft tissue. Cells from the supernatant were pelleted at 200×g for 6 minutes and collected in calcium-free DMEM supplemented with 100 micrograms/mL ascorbic acid, 10 mmol/L beta-glycerophosphate, 1 mmol/L calcium chloride, 1 mmol/L sodium pyruvate, 10% FCS, and antibiotics. Cells were plated at a concentration of $5\times10^5$ cells/mL in 35-mm six-well culture dishes, and the medium was changed every 48 hours. Cultures left untouched for 2-3 weeks developed cartilaginous nodules, which were picked up carefully, fixed with neutral buffered formalin, and routinely processed in paraffin for histological examination.

Alcian blue and hematoxylin-eosin (H&E) staining: Paraffin sections (6 microns) were deparaffinized in xylene, hydrated in graduated ethanols, and pretreated with 3% acetic acid for 3 minutes. Sections were then stained with 1% alcian blue at pH 2.5 for 30 minutes, thoroughly rinsed with tap water, and counterstained with H&E.

Morphometric analysis: Computerized analyses of the area size of cartilage-forming nodules, under control and IGF-I treated conditions, was performed on live cultures using an inverted microscope (Zeiss Axioskop 2), a video camera (CCD type, Princeton Instruments, Inc.), and IMAGE-PRO® PLUS software (Media Cybernetics, L. P., USA). Each figure in the morphometric studies represents a mean of 8-10 measurements performed on 3-5 different cultures. Significance was analyzed via Student's two-tailed t-test.

Immunohistochemistry: At the end of the incubation period the medium was removed and MCDC were washed twice with phosphate-buffered saline (PBS) solution, fixed with 4% paraformaldehyde, and permeabilized with 0.1% Triton X-100 in 5% normal goat serum for 5 minutes on ice. Quenching of endogenous peroxidase was performed using 3% hydrogen peroxide in methanol for 30 minutes at room temperature, following by blocking with 10% normal goat serum (Zymed Laboratories, South San Francisco, Calif.) for 20 minutes at room temperature. Cells were then incubated for 90 minutes with one of the following antibodies: rabbit anti IGF-I receptor (anti alpha-subunit, sc-712; Santa Cruz Biotechnology, Inc., Santa Cruz, Calif.), rabbit anti mouse type I collagen (AB765; CHEMICON International, Inc., Temecula, Calif.), mouse anti type II collagen (MAB8887; CHEMICON International), mouse anti type X collagen (clone X-AC9, MS-852-P; NeoMarkers, Lab Vision Corp., Fremont, Calif.), or mouse anti proliferating cell nuclear antigen (PCNA, 08-0110; Zymed). This was followed by incubation with an appropriate biotinylated second antibody, with streptavidin-peroxidase conjugate, and aminoethyl carbazole (AEC) as a substrate (Histostain-SP kit; Zymed); counterstaining was performed using hematoxylin.

Sodium dodecyl sulfate (SDS)-polyacrylamide gel electrophoresis (PAGE) and Western analysis: Cell lysates were prepared from pools of two or three confluent 35-mm plates cultured for 3, 5, 7, or 14 days. Cells were lysed with radioimmunoprecipitation assay (RIPA) buffer with freshly added protein inhibitors (250 microliters per $1\text{-}2\times10^6$ cells). Lysates (25 micrograms/lane) were separated by reducing SDS-PAGE and electrotransferred to nitrocellulose membrane. Blots were incubated with mouse anti type X collagen, detected by rabbit anti mouse horseradish peroxidase (Sigma), and developed using a chemiluminescence reagent (Renaissance® NEL105; New England Nuclear-Life Science Production, Boston, Mass.).

In situ hybridization: For in situ hybridization analysis, MCDC cells were cultured in eight-well "chamber slides" under the same conditions as described above for chondrocyte culture. At the end of the incubation period, the cells were fixed with 4% paraformaldehyde, treated with 3% hydrogen peroxide in methanol to neutralize endogenous peroxidase, incubated for 15 minutes with 2.5 micrograms/mL proteinase K, rinsed with 2 mg/mL glycine, and acetylated in 0.5% acetic anhydride in 0.1 M Tris at pH 8.0. Thereafter, cells were postfixed with 4% paraformaldehyde in PBS, and prehybridized for 10 minutes in 2×SSC and for 1 hour in hybridization buffer (50% formamide, 0.5 mg/mL salmon sperm DNA, 4×SSC, 1× Denhardt). Hybridization was performed for 18 hours at 42 degrees centigrade and maximal humidity with a 5 ng/microliter digoxigenin (DIG)-labeled probe (see below). At the end of the incubation period, slides were rinsed in SSC under increasingly stringent conditions and then with 0.1 molar Tris and 0.15 molar NaCl at pH 7.5. Hybrids were detected using anti DIG antibodies conjugated with peroxidase (F. Hoffmann-La Roche Ltd., Basel, Switzerland) and AEC as a substrate, and counterstained with hematoxylin.

Reverse transcriptase (RT)-polymerase chain reaction (PCR): cDNA was synthesized from 7 micrograms total RNA extracted from pooled tibiae and humerus bones derived from 18 day old ICR mouse embryos using SuperScript reverse transcriptase and oligo (dT) 12-18 primer (Invitrogen Life Technologies, RHENIUM Ltd., Jerusalem, Israel) in a 40 microliter reaction. In brief, RNA was incubated with 500 ng of oligo(dT)$_{12-18}$ in a volume of 25 microliters at 70 degrees centigrade for 10 minutes and cooled on ice. Then, 4 microliters of 100 millimolar dithiothreitol, 8 microliters of 5×first strand buffer, and 2 microliters of 10 mm each dNTPs were added. The reaction mixture was incubated for 2 minutes at 42 degrees centigrade, and 200 units of reverse transcriptase were added for an additional 55 minute incubation at 42 degrees centigrade, followed by inactivation of the enzyme at 95 degrees centigrade for 5 minutes. Subsequent PCR was performed using 4 microliters cDNA reaction mixture, 5 microliters of 1×PCR buffer, 8 microliters dNTPs 2.5 millimolar each, 100 ng each primer pair, and 1 unit Taq polymerase (Takara, Japan). Thirty cycles of amplification were performed as follows: incubation at 94 degrees centigrade for 1 minute, at 62 degrees centigrade for 1 minute, and at 72 degrees centigrade for 1 minute. The final polymerization incubation was performed at 72 degrees centigrade for 10 minutes. The primer sequences used for amplification of sequences encoding amino acids 55-266 of core-binding factor alpha1 (Cbfa1) were: 5'-GAGGGCACAAGTTC-TATCTGGA-3' (SEQ ID NO: 1) and 5'-GAGATTTGTGGGCCGGAGCGG-3' (SEQ ID NO: 2). The 633 bp DNA amplification product (SEQ ID NO: 3) encoding amino acids 55-266 of Cbfa1 was extracted and cloned into vector pUC57 using InsT/Aclone™ PCR product cloning kit (MBI Fermentas).

Digoxigenin-labeled antisense RNA probe for in situ hybridization: A 633 bp DNA fragment (SEQ ID NO: 3) encoding amino acids 55-266 of Cbfa1 cloned in vector pUC57 was linearized, and transcribed using SP6/T7 DIG-RNA labeling kit (Roche), according to the manufacturer's instructions, to generate a digoxigenin-labeled 633 base antisense RNA transcript (SEQ ID NO: 4) of the DNA sequence encoding amino acids 55-266 of Cbfa1, and as a negative control, a digoxigenin-labeled 633 base sense RNA transcript (SEQ ID NO: 5) of the DNA sequence encoding amino acids 55-266 of Cbfa1.

Northern analysis: Total RNA was extracted from cell cultures grown for 3 and 7 days using Tri Reagent (Molecular Research Center, Inc., Cincinnati, Ohio). RNA samples (23 micrograms/lane) were separated on 1.2% agarose gel and transferred to a nylon membrane. Cbfa1 transcript was detected by hybridization using a $^{32}$P-labeled 633-bp DNA fragment (SEQ ID NO: 3) encoding amino acids 55-266 of Cbfa1.

Experimental Results:

Early dedifferentiation and late redifferentiation of primary chondrocyte cultures: Chondrocytes were released from mandibular condyles obtained from 3 day old ICR mice by stepwise enzymatic separation. These MCDCs were plated at a concentration of $5\times10^5$ cells/mL. Morphological changes throughout 21 days of culture are depicted in phase-contrast photomicrographs (FIGS. 1a-d). After 18 hours, most cells displayed substrate attachment and a typically elongated fibroblast-like morphology (FIG. 1a). The cells proliferated rapidly, such that after 3 days the culture had become subconfluent. At this point the cells gradually lost their long processes (FIG. 1b). The 5 day old cultures were confluent, and the cells regained their chondrocytic polygonal shape with refractive contour (FIG. 1c). After 2 weeks in culture the cells began to aggregate, forming cartilaginous nodules (FIG. 1d). After 3 weeks the cultures contained numerous three-dimensional cartilaginous nodules. In order to examine the cellular population that occupied the nodules, several nodules were harvested, fixed, and processed for histological analysis. Sections were stained with H&E and acidic alcian blue dyes and analyzed, and as shown in FIGS. 2a-b, analysis of the sections revealed a multilayered nodular cartilage composition (FIG. 2a) comprising chondroblasts, chondrocytes, hypertrophic cells, and osteoblast-like cells (FIG. 2b), indicating that the late MCDC culture preserved its potential to follow morphological changes typical of the endochondral ossification cascade in-vitro.

Protein expression profile of long term primary chondrocyte cultures: In order to further characterize the developmental stages of the MCDC culture, the presence of gene products of several genes known to be upregulated during different stages of chondrocyte differentiation was examined immunohistochemically. Cultures of 1, 3, 7, and 14 days were fixed with paraformaldehyde, treated with Triton X-100, and reacted with antibodies against one of the following: PCNA, IGF-I receptors, and type I, II or X collagen. The results are shown in FIGS. 3a-h. Twenty-four hours after plating, the cells had started to proliferate intensively, as reflected by the high number of PCNA-positive cells (FIG. 3a). This proliferation was accompanied by loss of the typical chondrocyte morphology and by gain of a fibroblast-like phenotype (see FIGS. 1a-d). However, the cells remained sensitive to IGF-I. The 24 hour cultures exhibited high levels of IGF-I receptors (FIG. 3b). Three day old cultures produced mainly type I collagen (FIG. 3c) and only remnants of type II collagen (FIG. 3d). However, chondrocytes in the 7 day old cultures had stopped secreting type I collagen (FIG. 3e) and started to produce type II collagen instead (FIG. 3f). After 2 weeks in culture, large quantities of type II collagen were secreted into the extracellular matrix (FIG. 3g). The nodular cells of the 14 day old cultures produced type X collagen (FIG. 3h). For negative controls, parallel sections were incubated with the relevant (mouse or rabbit) non-immune serum following the same immunostaining procedure. No staining was detected in any of the controls (data not shown). Considering the overall immunohistochemical analysis of the developing culture, it appears that the MCDC underwent two distinct phases of differentiation in culture: a short dedifferentiation phase when cells lost their typical chondrocyte phenotype, followed by a prolonged redifferentiation phase when cells regained their positive reaction to collagen types II and X.

Morphometric studies were performed on MCDC cultures to compare the area of cartilage-forming nodules between the IGF-I treated and untreated cultures Increases in protein levels of type X collagen and decreases in Cbfa1 mRNA levels during MCDC culture correlate with chondrogenesis: In order to analyze chondrogenesis specific processes in the cultured MCDCs, changes in expression of the gene for type X collagen, a gene expressed relatively late in chondrogenesis by hypertrophic cells, and of the gene for Cbfa1, an early regulator of chondrogenesis/osteogenesis, were examined during the culture period. Changes in the levels of total type X collagen protein produced in the cultures were analyzed by immunoblotting analysis of lysates derived from 3, 5, 7, and 14 day old cultures (FIG. 4). Densitometry revealed a gradual increase in the levels of type X collagen throughout the first 2 weeks of development in culture, indicating increasing amounts of hypertrophic cells in the prolonged cultures.

Changes in the expression of Cbfa1 transcription factor were also examined. RNA samples extracted from pools of 3 and 7 day old cultures were separated on agarose gel and transferred to a nylon membrane. Cbfa1 transcript was detected by hybridization using a $^{32}$P-labeled 633-bp DNA fragment (SEQ ID NO: 3) encoding amino acids 55-266 of Cbfa1. Results are shown in FIG. 5. Densitometry of the Cbfa1 normalized to beta-actin levels revealed high levels of expression of Cbfa1 mRNA after 3 days in culture which dropped by 35% after 7 days in culture.

In situ hybridization performed on 3, 5, and 7 day old cultures, using as a probe a digoxigenin labeled 633 base antisense RNA transcript (SEQ ID NO: 4) of a DNA sequence encoding amino acid residues 55-266 of Cbfa1, confirmed the stage-dependent levels of Cbfa1 expression (FIGS. 6a-d). Levels of Cbfa1 in the 3 day old cultures were high (FIG. 6a), increased after 5 days of culture (FIG. 6b), and dropped markedly after 7 days of culture. The decrease in the expression of Cbfa1 correlates with chondrocyte specific maturation throughout the culture period.

Chondrogenesis stimulated by IGF-I in long term primary chondrocyte culture: Following the observation that cultured chondrocytes preserved their sensitivity to IGF-I (FIG. 3b), and since IGF-I is considered the major local regulator of chondrogenesis, the effects of IGF-I on the development of the MCDC cultures were examined (FIGS. 7a-f). Chondrocytes released from mandibular condyles were cultured in the presence or absence of $10^{-7}$ molar IGF-I for 3 days (FIGS. 7a-b) 7 days (FIGS. 7c-d) and 14 days (FIGS. 7e-f). At all stages, IGF-I treated cultures (FIGS. 7b, 7d and 7f) displayed greater development than untreated control cultures (FIGS. 7a, 7c and 7e). In the 3 day old IGF-I treated cultures, cells clustered to form primary cartilaginous nodules (7,685 plus or minus 380 square micrometers; FIG. 7b), which under control conditions appeared only after 7 days (FIG. 7c). The cartilaginous nodules produced by the 7 day old IGF-I treated cultures were significantly larger (22,950 plus or minus 645 square micrometers) than the untreated ones (8,320 plus or minus 550 square micrometers) (p less than 0.05). After 2 weeks of IGF-I treatment, well-developed cartilaginous nodules occupied most of the cultures (FIG. 7f), compared with relatively few nodules in the control cultures (FIG. 7e). The average size of cartilaginous nodules in the 2-week old IGF-I treated cultures was significantly higher (27,400 plus or minus 990 square micrometers) than those of the control cultures (15,688 plus or minus 855 square micrometers). The sensitivity to IGF-I confirmed that the MCDC culture was regulated similarly to that of the native epiphyseal chondrocytes.

Stimulation of early chondrogenesis specific stimulation of Cbfa-1 expression in early MCDC cultures by IGF-I: The effects of IGF-I on the expression of Cbfa1, one of the earliest markers of chondrogenic lineage, were examined by culturing MCDCs in the presence of IGF-I (FIGS. 8a-c). After 48 hours of treatment, $10^{-8}$ molar IGF-I (FIG. 8b) increased the expression of Cbfa1 over the control (FIG. 8a). This effect was further enhanced by $10^{-7}$ molar IGF-I (FIG. 8c), reaching levels of Cbfa1 resembling those achieved after 3 days under normal conditions (see FIG. 6a).

Discussion: The presently described results describe for the first time a late primary chondrocyte culture undergoing chondrogenesis. The mandibular condyle, from which the primary chondrocytes were derived, has been classified as a secondary cartilage since it differs from primary cartilage in its embryonic source (Durkin, J. F. et al., 1973. Oral Sci Rev 2:29-99; Menon, R. K. and Sperling, M. A., 1996. Endocrinol Metab Clin North Am 25:633-647). There is still debate as to whether the mandibular condyle arises from the periosteum of the growing mandible or from a programmed blastema (Spagnoli, A. and Rosenfeld, R. G., 1996. Endocrinol Metab Clin North Am 25:615-631). However, in all other aspects, mandibular condyles follow all the typical features of endochondral growth centers. The cellular population and matrix components thereof are similar to those found in the hyaline cartilage of epiphyseal growth centers. The condyle is composed of proliferating cartilage precursor cells, the chondroprogenitor cells, which upon ceasing proliferation differentiate into chondrocytes that secrete mainly type II collagen and aggrecan, the major cartilaginous matrix components. Chondrocytes then hypertrophy, producing type X collagen and calcified matrix, which is eventually replaced by bone (Fukada, K. et al, 1999. J Anat 195:321-329; Shibata, S. et al., 1997. J Anat 191:561-570).

It has previously been shown by the present inventors that chondrocytes of the mandibular condyle and the epiphyseal growth plate (EGP) are also similarly regulated under both physiological and pathological conditions. Condylar chondrocytes express receptors for growth hormone, IGF-I, and parathyroid hormone and react similarly to the EGP chondrocytes in type I diabetes and metabolic acidosis (Green, J., and Maor, G., 2000. Kidney Int 57:2258-2267; Maor, G. and Karnieli, E., 1999. Endocrinology 140:1841-1851). In the present study mandibular condyles of 3 day old mice were used as a source of chondrocyte culture. Condylar cells were separated by collagenase digestion into three successive fractions. The first cellular fraction contained mainly myocytes and perichondrium-derived fibroblast-like cells. The second fraction was an almost pure chondrocyte layer, and the third, deepest, fraction was a mixture of hypertrophic chondrocytes and remnants of the undigested material. The second cellular fraction was used for the primary chondrocyte culture. Cells, plated as a monolayer, were attached to the plate and started to proliferate. After 24 hours the cells lost their typical round chondrocyte shape and became elongated fibroblast-like cells producing mainly type I collagen.

The phenomenon of separated chondrocytes that undergo dedifferentiation upon plating as a monolayer, is quite common and well documented (Kergosien, N. et al., 1998. Calcif Tissue Int 62:114-121; Lemare, F. et al., 1998. J Cell Physiol 176:303-313). The loss of chondrocyte characteristics is probably due to the requirement of close cell-cell and cell-matrix interactions for maintenance of the chondrocyte phenotype. In order to regain the chondrocyte phenotype, various mechanical and biochemical methods have been used. Cells have been grown in micromass in alginate beads (Kulyk, W. M. et al., 2000. Exp Cell Res 255:327-332; Liu, H. et al., 1998. Biochim Biophys Acta 1425:505-515) or in the presence of FGF-2 or staurosporine (Benya, P. D. and Padilla, S. R., 1993. Exp Cell Res 204:268-277). However, in the presently described studies tissue culture underwent spontaneous redifferentiation as the culture became confluent. After 5-7 days of incubation, the cells gradually regained their polygonal shape and type II collagen production. The spontaneous chondrogenesis that occurred in the presently described model was probably due to two main factors: the source of the cells and the special culturing conditions. The neonatal-derived condylar chondrocytes had a very high rate of proliferation that resulted in a very rapid confluent culture. These cells were cultured under permissive conditions that included mainly ascorbic acid, beta-glycerophosphate, and pyruvate. Moreover, the source of the chondroblasts, the neonatal mandibular condyle, is highly active in endochondral ossification. Thus, such cells are potentially cartilage precursor cells and undergo spontaneous chondrogenesis. The expression of Cbfa1 in the "young" 3 day old cultures was high and dropped dramatically in the 7 day old culture.

Cbfa1 is a transcription factor that is essential for proper chondrogenesis as well as osteogenic processes (Inada, M. et al., 1999. Dev Dyn 214:279-290). As culture differentiation progresses, chondrocytes begin to cluster, forming cartilaginous nodules with morphological characteristics of cartilaginous growth centers, including hypertrophic cells embedded in a highly metachromatic matrix. This developmental process is accompanied by production of increasing amounts of type X collagen, indicating hypertrophy processes occurring in the developing cultures (Chen, Q. et al., 1992. Bone Miner 17:223-227). Developing chondrocytes are also characterized by their sensitivity to various factors that regulate the chondrogenic process. One of the major local growth factors regulating chondrocyte differentiation is IGF-I (Isgaard, J., 1992. Growth Regul 2:16-22).

The presently described results show that the newly cultured chondrocytes continued producing IGF-I receptor, despite undergoing an early phase of dedifferentiation. The preservation of sensitivity of MCDC cells to IGF-I enabled its use in order to further enhance chondrogenesis. It was possible to show that culturing in the presence of $10^{-7}$ molar IGF-I increased the rate of chondrogenesis at any stage of development, thus providing a tool for controlling the developmental rate of the culture. This inducing effect of IGF-I is probably mediated by regulation of the expression of Cbfa1, a transcription factor that belongs to the runt family and plays a major role in chondrogenesis (Inada, M. et al., 1999. Dev Dyn 214:279-290). The capacity of the primary culture to form cartilaginous nodules was maintained until the third to fourth passages; each time, cells underwent dedifferentiation and spontaneous redifferentiation. From the fourth to the fifth passages, cells redifferentiated into polygonal chondrocytes producing type II collagen, but no longer piled up to form cartilaginous nodules (data not shown). These "senescent" cultures were very reminiscent of articular cartilage-derived cultures and may, in fact, also serve as a model for studies exploring various articular pathologies.

Hence, the presently described culture conditions can be used for the first time for generating a model for primary monolayer chondrocyte culture, from neonatal-derived mandibular condyles, that undergoes spontaneous chondrogenesis and that may be used as a model for studies concerning regulatory mechanisms of endochondral ossification. This chondrocyte model might also be used for studies concerning mechanisms involved in various articular pathologies, as well as different metabolic disorders affecting normal skeletal growth such as type I diabetes.

Conclusion: The presently described results describe a novel and unique method of generating isolated mandibular condyles depleted of fibroblast-like cells and myocytes and comprising chondrocytes, a novel and unique method of isolating mandibular condyle chondrocytes, and a novel and unique method of culturing primary chondrocytes so as to generate optimally differentiated cultured chondrocytes/endochondral bone cells. The presently described culturing method enables generation of optimally differentiated cultured chondrocytes/endochondral bone cells from primary isolated chondrocytes under optimal and unique culturing conditions which are devoid of a three-dimensional/biomolecule-coated support, which employ a culture medium devoid of a non-serum derived supplement such as a protein kinase inhibitor, microfilament modifying compound or polypeptide growth factor, and which include culturing of non-confluent chondrocytes under normoxic culturing conditions. By virtue of enabling generation of optimally differentiated cultured chondrocytes/bone, the presently described chondrocyte isolation and culturing methods can be used for optimally generating cultured chondrocytes/bone having optimal utility for treating cartilage/bone diseases, for testing cartilage/bone disease drugs/treatment methods in-vitro, and for modeling processes of normal and pathogenic growth and differentiation of cartilage and bone in-vitro.

Example 2

Genetic Transformation of Isolated Mandibular Condyle Derived Chondrocytes

Materials and Methods:

The capacity to genetically transform cultured mandibular condyle derived chondrocytes (MCDCs) isolated as described in Example 1, above, would be potentially highly useful in therapeutic applications involving cell therapy with such cells and for investigating chondrocyte biology in-vitro.

Constructs: Sequences encoding osteoprotegerin (OPG) were cloned into expression vector pIRES2-EGFP (Clontech) yielding the bicistronic expression vector OPG-IRES-GFP for co-expression of osteoprotegerin and green fluorescent protein (GFP) to thereby generate expression construct pcDNAI-OPG-IRES-GFP. Sequences encoding a fusion protein composed of GFP fused to glucose transporter GLUT4 were cloned into expression vector pcDNAneoI to thereby generate expression vector pcDNAI-GLUT4-GFP.

Transfection of cultured mandibular condyle derived chondrocytes: MCDCs were cultured in 24-well plates at a concentration of $3 \times 10^5$ cells/ml for 24 hours. The cells were pretreated with 20 units/ml hyaluronidase for 1 hour in the presence of 5% fetal calf serum (FCS) and transfected using 1 microgram of transforming expression vector DNA per well using the JetPEI transfection kit (poly plus Transfection, France) using a 6 hour incubation, according to the manufacturer's instructions, in the presence of hyaluronidase.

Experimental Results:

In order to demonstrate the transfectability of the MCDCs isolated as described in Example 1 above, MCDCs were transfected with construct pcDNAI-OPG-IRES-GFP for co-expression of OPG and GFP, or with construct pcDNAI-GLUT4-GFP for expression of a GLUT-GFP fusion protein. As is shown in FIG. 9, the cultured MCDCs were successfully transfected, as evidenced by the appearance of numerous (about 1-5%) GFP positive cells 24 hours post-transfection.

Conclusion: Cultured MCDCs isolated as described in Example 1 above can be genetically transformed to express desired polynucleotides/genes. As such, the genetically transformed cultured MCDCs of the present invention have significant utility in therapeutic applications and for investigating chondrocyte biology in-vitro.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, patent applications and sequences identified by their accession numbers mentioned in this specification are herein incorporated in their entirety by reference into the specification, to the same extent as if each individual publication, patent, patent application or sequence identified by its accession number was specifically and individually indicated to be incorporated herein by reference. In addition, citation or identification of any reference in this application shall not be construed as an admission that such reference is available as prior art to the present invention.

What is claimed is:

1. A method of generating cultured chondrocytes, the method comprising:
   (a) isolating chondrocytes from mandibular condyle tissue of a neonatal mammal; and
   (b) culturing said isolated chondrocytes, wherein said culturing comprises plating said isolated chondrocytes as a monolayer in a culturing medium supplemented with serum, ascorbic acid, β glycerophosphate, calcium chloride and pyruvate and culturing said isolated chondrocytes for at least 7 days, thereby generating the cultured chondrocytes, wherein the cultured chondrocytes express collagen Type II and not collagen Type I.

2. The method of claim 1, wherein step (a) comprises:
   (c) selectively removing fibroblast-like cells and/or myocytes from said mandibular condyle tissue, thereby generating modified mandibular condyle tissue depleted of said fibroblast-like cells and/or said myocytes, said modified mandibular condyle tissue including chondrocytes; and
   (d) selectively isolating said chondrocytes from said modified mandibular condyle tissue.

3. The method of claim 2, wherein step (c) is effected by incubating said mandibular condyle tissue with a protease.

4. The method of claim 2, wherein step (d) is effected by incubating said modified mandibular condyle tissue with a protease so as to selectively release chondrocytes therefrom.

5. The method of claim 4, further comprising isolating said chondrocytes released from said modified mandibular condyle tissue.

6. The method of claim 1, wherein step (b) is under normoxic conditions.

7. The method of claim 1, wherein step (b) is effected under culturing conditions which include culturing a subconfluent population of said isolated chondrocytes.

8. The method of claim 1, wherein step (b) is effected for a minimum duration selected from a range of 14-21 days.

9. The method of claim 1, wherein step (b) includes passaging said cultured chondrocytes a predetermined number of times.

10. The method of claim 9, wherein said predetermined number of times is up to four times.

11. The method of claim 1, wherein the cultured chondrocytes are cultured primary chondrocytes.

* * * * *